United States Patent
Sano et al.

(10) Patent No.: US 10,507,437 B2
(45) Date of Patent: Dec. 17, 2019

(54) GAS SEPARATION MEMBRANE, GAS SEPARATION MODULE, GAS SEPARATION APPARATUS, AND GAS SEPARATION METHOD

(71) Applicant: FUJIFILM Corporation, Tokyo (JP)

(72) Inventors: Satoshi Sano, Kanagawa (JP); Koji Hironaka, Kanagawa (JP); Keisuke Kodama, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 197 days.

(21) Appl. No.: 15/679,159

(22) Filed: Aug. 17, 2017

(65) Prior Publication Data

US 2018/0021741 A1 Jan. 25, 2018

Related U.S. Application Data

(63) Continuation of application No. PCT/JP2016/052926, filed on Feb. 1, 2016.

(30) Foreign Application Priority Data

Feb. 27, 2015 (JP) ................... 2015-039092

(51) Int. Cl.
*C08G 77/20* (2006.01)
*C08G 77/28* (2006.01)
(Continued)

(52) U.S. Cl.
CPC ............. *B01D 71/70* (2013.01); *B01D 53/22* (2013.01); *B01D 53/228* (2013.01);
(Continued)

(58) Field of Classification Search
CPC ...... B01D 53/22; B01D 53/228; B01D 71/10; B01D 71/12; B01D 71/16; B01D 71/70;
(Continued)

(56) References Cited

U.S. PATENT DOCUMENTS 4,964,887 A * 10/1990 Shimatani ............. B01D 53/22
208/308
5,177,131 A * 1/1993 Takago ............. B01D 67/0048
524/100
(Continued)

FOREIGN PATENT DOCUMENTS

JP S58-40102 3/1983
JP S61-120617 6/1986
(Continued)

OTHER PUBLICATIONS

English language machine translation for JP 2014-176795. Retrieved from http://translationportal.epo.org on May 7, 2019. (Year: 2019).*

(Continued)

*Primary Examiner* — Jason M Greene
(74) *Attorney, Agent, or Firm* — JCIPRNET

(57) ABSTRACT

A gas separation membrane has a gas separation layer containing a cellulose resin, and an organopolysiloxane compound layer disposed on the gas separation layer in which Si ratio of the organopolysiloxane compound layer after immersion in chloroform to the organopolysiloxane compound layer before immersion in chloroform, the Si ratio being calculated by Mathematical expression (I), is 0.6 to 1.0.

Si ratio=(Si—Kα X-ray intensity after immersion in chloroform)/(Si—Kα X-ray intensity before immersion in chloroform)  Mathematical expression (I)

18 Claims, 1 Drawing Sheet

(51) Int. Cl.
| | |
|---|---|
| *B01D 71/70* | (2006.01) |
| *B01D 53/22* | (2006.01) |
| *B01D 69/12* | (2006.01) |
| *B32B 27/00* | (2006.01) |
| *B01D 61/36* | (2006.01) |
| *B01D 71/12* | (2006.01) |
| *C10L 3/10* | (2006.01) |
| *B01D 69/02* | (2006.01) |
| *B01D 69/10* | (2006.01) |
| *C07C 7/144* | (2006.01) |
| *C08L 1/12* | (2006.01) |
| *C08L 1/14* | (2006.01) |
| *C09D 183/06* | (2006.01) |
| *B01D 71/10* | (2006.01) |
| *C01B 32/55* | (2017.01) |
| *B01D 53/14* | (2006.01) |
| *C07C 9/04* | (2006.01) |
| *C08B 3/00* | (2006.01) |
| *C08G 77/04* | (2006.01) |

(52) U.S. Cl.
CPC ........... *B01D 61/364* (2013.01); *B01D 69/02* (2013.01); *B01D 69/10* (2013.01); *B01D 69/12* (2013.01); *B01D 71/12* (2013.01); *B32B 27/00* (2013.01); *C07C 7/144* (2013.01); *C08L 1/12* (2013.01); *C08L 1/14* (2013.01); *C09D 183/06* (2013.01); *C10L 3/104* (2013.01); *B01D 53/1475* (2013.01); *B01D 71/10* (2013.01); *B01D 2256/22* (2013.01); *B01D 2256/245* (2013.01); *B01D 2257/504* (2013.01); *B01D 2257/7025* (2013.01); *B01D 2258/05* (2013.01); *B01D 2325/023* (2013.01); *B01D 2325/04* (2013.01); *C01B 32/55* (2017.08); *C07C 9/04* (2013.01); *C08B 3/00* (2013.01); *C08G 77/04* (2013.01); *C08G 77/20* (2013.01); *C08G 77/28* (2013.01); *C08L 2312/06* (2013.01); *C10L 2290/548* (2013.01); *Y02C 10/10* (2013.01); *Y02C 20/20* (2013.01); *Y02P 20/152* (2015.11); *Y02P 20/156* (2015.11)

(58) Field of Classification Search
CPC .......... B01D 2257/504; B01D 2323/30; C10L 3/104; C09D 183/06
See application file for complete search history.

(56) References Cited

U.S. PATENT DOCUMENTS

| | | | |
|---|---|---|---|
| 5,428,123 A * | 6/1995 | Ward | B01D 69/08 210/500.21 |
| 6,368,382 B1 | 4/2002 | Chiou | |
| 8,816,003 B2 | 8/2014 | Liu et al. | |
| 2005/0145107 A1* | 7/2005 | Kessler | B01D 53/228 95/45 |
| 2010/0270234 A1 | 10/2010 | Liu et al. | |
| 2013/0255490 A1* | 10/2013 | Matteucci | B01D 53/228 95/51 |
| 2014/0345462 A1* | 11/2014 | Itou | B01D 69/12 96/13 |
| 2015/0376365 A1* | 12/2015 | Halbach | B01D 71/70 521/64 |
| 2017/0043303 A1* | 2/2017 | Hong | B01D 71/70 |
| 2017/0210101 A1* | 7/2017 | Peinemann | B01D 67/0079 |

FOREIGN PATENT DOCUMENTS

| | | | | |
|---|---|---|---|---|
| JP | S62-183837 | | 8/1987 | |
| JP | S62-216624 | | 9/1987 | |
| JP | H02-35922 | | 2/1990 | |
| JP | H04-317734 | | 11/1992 | |
| JP | H06-269650 | | 9/1994 | |
| JP | 2005-169243 | | 6/2005 | |
| JP | 2007-297605 | | 11/2007 | |
| JP | 2014-176795 | * | 9/2014 | ............ B01D 53/22 |

OTHER PUBLICATIONS

"International Search Report (Form PCT/ISA/210) of PCT/JP2016/052926", with English translation thereof, dated Apr. 26, 2016, pp. 1-4.

"Written Opinion (Form PCT/ISA/237) of the International Searching Authority of PCT/JP2016/052926", dated Apr. 26, 2016, with English translation thereof, pp. 1-10.

"Office Action of Japan Counterpart Application" with English translation thereof, dated Jan. 9, 2018, p. 1-p. 7.

* cited by examiner

GAS SEPARATION MEMBRANE, GAS SEPARATION MODULE, GAS SEPARATION APPARATUS, AND GAS SEPARATION METHOD

CROSS-REFERENCE TO RELATED APPLICATIONS

This application is a Continuation of PCT International Application No. PCT/JP2016/052926, filed on Feb. 1, 2016, which claims priority under 35 U.S.C. § 119(a) to Japanese Patent Application No. 2015-039092, filed on Feb. 27, 2015. Each of the above application(s) is hereby expressly incorporated by reference, in its entirety, into the present application.

BACKGROUND OF THE INVENTION

1. Field of the Invention

The present invention relates to a gas separation membrane, a gas separation module, a gas separation apparatus, and a gas separation method.

2. Description of the Related Art

Materials formed of polymer compounds each have gas permeability specific to the constituent materials. On the basis of this property, it is possible to cause selective permeation and separation of a desired gas component by using a membrane formed of a particular polymer compound. Regarding industrial applications of such a gas separation membrane, in relation to the issues of global warming, separation and recovery of carbon dioxide from large-scale sources of carbon dioxide emission have been examined in thermal power plants, cement plants, blast furnaces in steel mills, and the like. Furthermore, this membrane separation technique has been attracting attention as means capable of solving environmental problems with relatively low energy.

In addition, natural gas and biogas (gas generated by fermentation or anaerobic digestion of excrement of organisms, organic fertilizers, biodegradable substances, sewage, garbage, and energy crops) are mixed gas containing mainly methane and carbon dioxide, and a membrane separation method has been examined as means for removing impurities such as carbon dioxide in such mixed gas (Japanese Patent Application Publication No. 2007-297605).

In order to realize a practical gas separation membrane, it is necessary to reliably obtain sufficient gas permeability by forming a gas separation layer as a thin layer. An example of the method therefor is a method that includes forming a polymer compound into an asymmetric membrane by a phase separation process, so that a portion that contributes to separation is formed as a thin layer referred to as a dense layer or a skin layer. In this asymmetric membrane, the dense layer is allowed to function as a gas separation layer, and a portion other than the dense layer is allowed to function as a support layer which provides the membrane with mechanical strength.

Besides the asymmetric membrane, a form of a composite membrane is also known in which a material which provides a gas separation function and a material which provides mechanical strength are different from each other. This composite membrane has a structure in which a gas separation layer that is a thin layer formed of a polymer compound is formed on a gas-permeable support which provides mechanical strength.

However, when the thickness of a gas separation layer is reduced, defects tend to be generated by rubbing, folding, or the like. The generation of membrane defects may cause a significant decrease in the gas separation performance. It has been reported that a protective layer has been provided on a gas separation layer in order to solve this problem. For example, the specification of U.S. Pat. No. 6,368,382 discloses that an asymmetric membrane is coated with an epoxysilicone cured by ultraviolet rays to improve the performance of the membrane.

In the case where a gas separation membrane is used in actual plants, the membrane is plasticized by, for example, the influence of high-pressure conditions and impurities (for example, benzene, toluene, and xylene) that are present in natural gas, resulting in a problem of a decrease in separation selectivity. It is known that introducing a crosslinked structure or a branched structure to a polymer compound that forms a gas separation layer is effective for suppressing this plasticization of the membrane (for example, the specification of U.S. Patent Application Publication No. 2010/0270234 and the specification of U.S. Pat. No. 8,816,003).

SUMMARY OF THE INVENTION

The introduction of the crosslinked structure to a polymer compound that forms a gas separation layer is effective for suppressing plasticization of the gas separation layer caused by impurity components, such as toluene and the like, which are present in natural gas. However, in gas separation, for example, under conditions of a high temperature, a high pressure, and a high humidity, as in gas separation in a natural gas field, even when the crosslinked structure is introduced, it is difficult to prevent plasticization of a membrane. Thus, there has been a desire for a technique for realizing both gas permeability and gas separation selectivity at a higher level.

An object of the present invention is to provide a gas separation membrane exhibiting good gas separation selectivity in addition to good gas permeability, being unlikely to be plasticized and exhibiting a good gas separation performance, even when used under conditions of a high temperature, a high pressure, and a high humidity, being unlikely to be affected by impurity components, such as toluene and the like, which are present in natural gas, having good folding endurance and being capable of being processed into various module forms, and being capable of being produced at a high yield. Another object of the present invention is to provide a gas separation module, a gas separation apparatus, and a gas separation method using the gas separation membrane.

In view of the above problems, the inventors of the present invention conducted extensive research. As a result, the inventors found that a gas separation membrane in which a layer formed of organopolysiloxane compounds linked through a particular linking structure is disposed on a gas separation layer exhibits good gas permeability and gas separation selectivity even under conditions of a high temperature, a high pressure, and a high humidity, exhibits good resistance to impurity components such as toluene, has sufficiently good folding endurance such that membrane defects are unlikely to be generated even when the membrane is folded repeatedly, and has a high yield and is good in terms of production efficiency. Further research that was conducted on the basis of these findings led to the completion of the present invention.

Specifically, the above objects of the present invention have been achieved by means described below.

A first aspect of the present invention provides a gas separation membrane having a gas separation layer containing a cellulose resin, and an organopolysiloxane compound layer disposed on the gas separation layer. A Si ratio of the organopolysiloxane compound layer after immersion in chloroform to the organopolysiloxane compound layer before immersion in chloroform, the Si ratio being calculated by Mathematical expression (I), is 0.6 to 1.0.

Si ratio=(Si—Kα X-ray intensity after immersion in chloroform)/(Si—Kα X-ray intensity before immersion in chloroform)    Mathematical expression (I)

The organopolysiloxane compound layer preferably has a structure in which organopolysiloxane compounds are linked to each other through a linking group selected from *—O-M-O—*, *—S-M-S—*, *—NR$^a$C(=O)—*, *—NR$^b$C(=O)NR$^b$—*, *—O—CH$_2$—O—*, *—S—CH$_2$CH$_2$—*, *—OC(=O)O—*, *—CH(OH)CH$_2$OCO—*, *—CH(OH)CH$_2$O—*, *—CH(OH)CH$_2$S—*, *—CH(OH)CH$_2$NR$^c$—*, *—CH(CH$_2$OH)CH$_2$CO—*, *—CH(CH$_2$OH)CH$_2$O—*, *—CH(CH$_2$OH)CH$_2$S—*, *—CH(CH$_2$OH)CH$_2$NR$^c$—*, *—CH$_2$CH$_2$—*, *—C(=O)O$^-$N$^+$(R$^d$)$_3$—*, *—SO$_3$$^-$N$^+$(R$^e$)$_3$—*, and *—PO$_3$H$^-$N$^+$(R$^f$)$_3$—*, and the organopolysiloxane compound layer preferably contains 10 to 5,000 ppm of an organic solvent. In the formulae, M represents a divalent to tetravalent metal atom; R$^a$, R$^b$, R$^c$, R$^d$, R$^e$, and R$^f$ each independently represent a hydrogen atom or an alkyl group; and the symbol * represents a linking site.

The metal atom M is preferably a metal atom selected from Be, Mg, Ca, Sc, Y, Ti, Zr, V, Cr, Mo, Mn, Fe, Co, Ni, Cu, Zn, B, Al, Ga, and In.

The linking group is preferably a linking group selected from *—O-M$^1$-O—*, *—S-M$^1$-S—*, *—O—CH$_2$—O—*, *—S—CH$_2$CH$_2$—*, *—OC(=O)O—*, *—CH$_2$CH$_2$—*, and *—C(=O)O$^-$N$^+$(R$^d$)$_3$—*. In the formulae, M$^1$ represents a metal atom selected from Zr, Fe, Zn, B, Al, and Ga; and R$^d$ represents a hydrogen atom or an alkyl group.

The organopolysiloxane compound layer preferably has a structure in which organopolysiloxane compounds are linked to each other through a linking group selected from *—O-M$^1$-O—* and *—S-M$^1$-S—* and a structure in which organopolysiloxane compounds are linked to each other through a linking group selected from *—O—CH$_2$—O—*, *—S—CH$_2$CH$_2$—*, *—OC(=O)O—*, *—CH$_2$CH$_2$—*, and *—C(=O)O$^-$N$^+$(R$^d$)$_3$—*.

The organopolysiloxane compound layer preferably has at least one structure selected from (a) or (b).

(a) A structure having a structure represented by General formula (1) and a structure represented by General formula (2) or General formula (3)

(b) A structure represented by General formula (4)

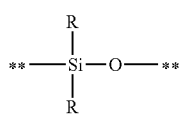

General formula (1)

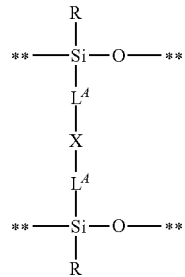

General formula (2)

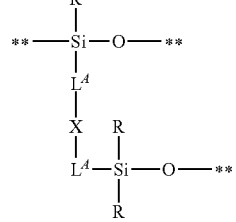

General formula (3)

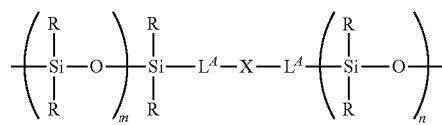

General formula (4)

In the formulae, R represents an alkyl group or an aryl group; L$^A$ represents a single bond or a divalent linking group; X represents a linking group selected from *—O-M$^1$-O—*, *—S-M$^1$-S—*, *—O—CH$_2$—O—*, *—S—CH$_2$CH$_2$—*, *—OC(=O)O—*, *—CH$_2$CH$_2$—*, and *—C(=O)O$^-$N$^+$(R$^d$)$_3$—* where M$^1$ represents Zr, Fe, Zn, B, Al, or Ga; R$^d$ represents a hydrogen atom or an alkyl group; m and n are each an integer of 2 or more; the symbol * represents a linking site; and the symbol * represents a linking site in a siloxane bond.

The structure of (a) preferably further has a repeating unit represented by Formula (5).

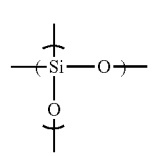

Formula (5)

A content ratio of the repeating unit represented by Formula (5) in the organopolysiloxane compound layer is preferably 0.01 to 0.55.

The metal atom M is preferably B or Al.

The metal atom M$^1$ is preferably B or Al.

The cellulose resin contained in the gas separation layer is preferably a cellulose resin having a repeating unit represented by Formula (A):

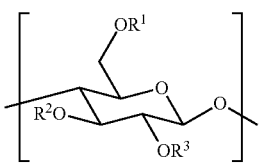

(A)

where $R^1$, $R^2$, and $R^3$ each independently represent a group selected from a hydrogen atom, an alkyl group, and an acyl group.

The gas separation membrane is preferably an asymmetric membrane.

The gas separation membrane preferably has a thickness of 10 to 200 μm.

The gas separation membrane is preferably the asymmetric membrane supported by a nonwoven fabric.

The gas separation membrane is preferably used for selectively allowing permeation of carbon dioxide from gas containing carbon dioxide and methane.

A second aspect of the present invention provides a gas separation module using the gas separation membrane according to the first aspect.

A third aspect of the present invention provides a gas separation apparatus including the gas separation module according to the second aspect.

A fourth aspect of the present invention provides a gas separation method including using the gas separation membrane according to the first aspect.

The gas separation method according to the fourth aspect preferably includes selectively allowing permeation of carbon dioxide from gas containing carbon dioxide and methane.

Herein, when a plurality of substituents, linking groups, or the like (hereinafter referred to as substituents or the like) represented by specific symbols are present or a plurality of substituents or the like are defined simultaneously or alternatively, the substituents or the like may be the same or different from each other. The same applies to the definition of the number of substituents or the like. When a formula includes a plurality of repeated partial structures represented by the same expression, the partial structures or the repeating units may be the same or different from each other. In addition, even if not specifically stated, when a plurality of substituents or the like are close (in particular, adjacent) to each other, they may be linked or fused to each other to form a ring.

With regard to expressing compounds used herein, the expression includes salts thereof and ions thereof in addition to the compounds. Furthermore, the expression includes derivatives formed by changing a part of the structure within the range in which desired effects are achieved. Herein, a substituent (the same applies to a linking group) in which substitution or no substitution is not specified may have any substituent within the range in which desired effects are achieved. The same applies to a compound in which substitution or no substitution is not specified.

The preferable range of substituents used herein includes groups selected from Group Z of substituents described below, unless otherwise stated.

The gas separation membrane, the gas separation module, and the gas separation apparatus of the present invention have good gas separation selectivity in addition to good gas permeability, exhibit a good gas separation performance, even when used under conditions of a high temperature, a high pressure, and a high humidity, and are less likely to be affected by impurity components, such as toluene and the like, which are present in natural gas. In addition, the gas separation membrane of the present invention has a high yield and is good in terms of production efficiency. Furthermore, the gas separation membrane of the present invention has good folding endurance and can be processed into various module forms.

According to the gas separation method of the present invention, gas can be separated with good gas permeability and good gas separation selectivity even under conditions of a high temperature, a high pressure, and a high humidity. Furthermore, according to the gas separation method of the present invention, a good gas separation performance is maintained even under the presence of impurities, such as toluene and the like, which can be present in gas.

DESCRIPTION OF THE PREFERRED EMBODIMENTS

Figure 1:
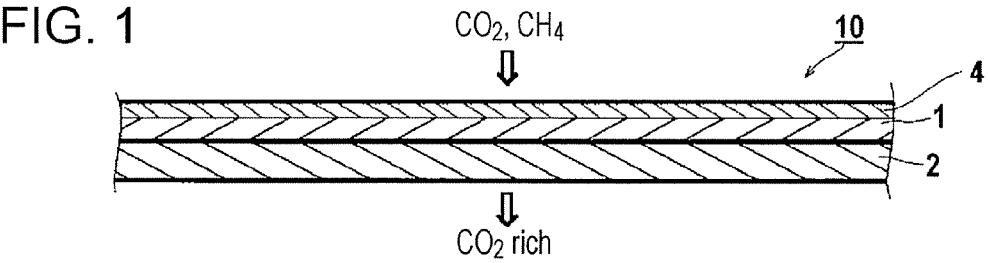
FIG. 1 is a schematic sectional view illustrating a gas separation membrane according to a preferred embodiment (composite membrane) of the present invention.

A gas separation membrane of the present invention has a gas separation layer containing a cellulose resin. Furthermore, an organopolysiloxane compound layer having a Si ratio in a particular range is disposed on the gas separation layer, the Si ratio being a Si ratio of the siloxane compound layer after immersion in chloroform to the siloxane compound layer before immersion in chloroform.

The gas separation membrane of the present invention may have a form of an asymmetric membrane or a form of a composite membrane.

The gas separation membrane of the present invention will be described in detail. The term "siloxane compound" used herein refers to an "organopolysiloxane compound" unless otherwise stated. Similarly, the term "siloxane compound layer" used herein refers to an "organopolysiloxane compound layer" unless otherwise stated.

Gas Separation Layer

In the gas separation membrane of the present invention, the cellulose resin that forms the gas separation layer is not particularly limited, and cellulose resins having various substituents can be used as the cellulose resin. In particular, a cellulose resin having a repeating unit represented by Formula (A) is preferable.

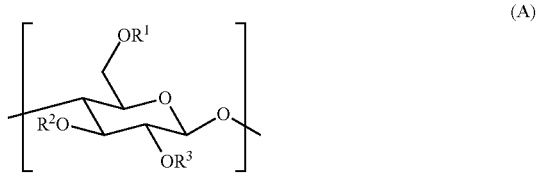

(A)

In the formula, $R^1$, $R^2$, and $R^3$ each independently represent a group selected from a hydrogen atom, an alkyl group (the alkyl group is preferably an alkyl group having 1 to 10 carbon atoms, more preferably an alkyl group having 1 to 5 carbon atoms, and still more preferably an alkyl group having 1 to 3 carbon atoms, and preferred specific examples thereof include alkyl groups cited in Group Z of substituents described below), and an acyl group (the acyl group is preferably an acyl group having 2 to 12 carbon atoms, more preferably an acyl group having 2 to 10 carbon atoms, still more preferably an acyl group having 2 to 8 carbon atoms, and even still more preferably an acyl group having 2 to 5 carbon atoms, and preferred specific examples thereof include acyl groups cited in Group Z of substituents described below).

When $R^1$, $R^2$, and $R^3$ are each an alkyl group or an acyl group, the alkyl group or the acyl group may further have a substituent.

Examples of the cellulose resin formed by a repeating unit represented by General formula (A) above include P-1 to P-20 shown below. However, the present invention is not limited thereto. In the examples shown below, d represents the degree of substitution (maximum value: 3.0), Ph represents phenyl, Ac represents acetyl, Me represents methyl, and HP represents hydroxypropyl.

The number of repeating units in P-1 to P-20 below may be, for example, 10 to 10,000.

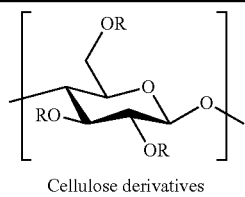

Cellulose derivatives

| | |
|---|---|
| P-1 | R = H, COCH$_3$, d < 2.0 |
| P-2 | R = H, COCH$_3$, d = 2.19 |
| P-3 | R = H, COCH$_3$, d = 2.44 |
| P-4 | R = H, COCH$_3$, d = 2.86 |
| P-5 | R = H, COCH$_3$, COCH$_2$CH$_3$ |
| P-6 | R = H, COCH$_3$, COPh |
| P-7 | R = H, COCH$_3$, COPh |
| P-8 | R = H, CH$_2$CH$_3$, d = 2.1 |
| P-9 | R = H, CH$_3$, CH$_2$CH$_2$OH |
| P-10 | R = H, CH$_3$, CH$_2$CH(OH)CH$_3$ |
| P-11 | R = H, CH$_3$, CH$_2$CH$_3$, CH$_2$CH$_2$OH |
| P-12 | R = H, CH$_2$CH$_2$OH |
| P-13 | R = H, CH$_2$CH$_2$OH, CH$_2$CH$_2$OAc |
| P-14 | R = H, CH$_2$CO$_2$H |
| P-15 | R = H, COCH$_3$, COC$_6$H$_4$CO$_2$H |
| P-16 | R = H, CH$_3$, CH$_2$CH(OAc)CH$_3$ |
| | DS(Me/HP-Ac/Ac = 1.5/0.2/1.3 |
| P-17 | R = H, CH$_3$, COCH$_3$, CH$_2$CH$_2$OCOCH$_3$ |
| P-18 | R = H, CH$_3$, COCH$_3$ |
| P-19 | R = H, CH$_3$, CH$_2$CH$_3$ |
| P-20 | R = H, COCH$_3$, CH$_2$CH$_3$ |

A molecular weight of the cellulose resin before formation of crosslinking, the cellulose resin being used in the present invention, is preferably 10,000 to 1,000,000, more preferably 15,000 to 500,000, and still more preferably 20,000 to 200,000 in terms of weight-average molecular weight.

The terms "molecular weight" and "dispersity" used herein refer to values determined by gel permeation chromatography (GPC) unless otherwise stated, and the term "molecular weight" refers to a weight-average molecular weight in terms of polystyrene. The measurement conditions are as follows.

Type of column used: TOSOH TSKgel Super AWM-H (6.0 mm ID×15 cm)
Number of columns used: 3
Type of solvent: N-methylpyrrolidone
Flow rate of solvent: 0.5 mL/min.
Measurement temperature: 40° C.
Apparatus: TOSOH EcoSEC HLC-8320GPC It is also preferable that the cellulose resin form a crosslinked structure in the gas separation layer.

Siloxane Compound Layer

In the gas separation membrane of the present invention, a siloxane compound layer is disposed on the gas separation layer so as to be in contact with the gas separation layer. The siloxane compound layer has a Si ratio in the range of 0.6 to 1.0, the Si ratio being a Si ratio of the siloxane compound layer after immersion in chloroform to the siloxane compound layer before immersion in chloroform and represented by Mathematical expression (I).

$$\text{Si ratio} = (\text{Si—K}\alpha \text{ X-ray intensity after immersion in chloroform})/(\text{Si—K}\alpha \text{ X-ray intensity before immersion in chloroform}) \quad \text{Mathematical expression (I)}$$

The Si ratio is determined by irradiating a surface of a siloxane compound layer with X-rays before and after immersion of the siloxane compound layer in chloroform at 25° C. for 12 hours, and measuring the intensity of the Si—Kα X-ray (1.74 keV). The method for measuring the Si—Kα X-ray intensity is described in, for example, Japanese Unexamined Patent Application Publication No. 6-88792. Specifically, the Si—Kα X-ray intensity of a gas separation membrane after immersion in chloroform and the Si—Kα X-ray intensity of the gas separation membrane before immersion are measured. A decrease in the Si—Kα X-ray intensity after immersion compared with the Si—Kα X-ray intensity before the immersion means that a low-molecular weight siloxane compound component (low-molecular weight component), a non-crosslinked siloxane compound component, and a low-crosslinked siloxane component are present in the siloxane compound layer and these components have dissolved into chloroform. Accordingly, a lower degree of the decrease in the Si—Kα X-ray intensity after immersion in chloroform means that the crosslinking density of the polymer that forms the siloxane compound layer increases and the polymer is less likely to be dissolved into chloroform.

The organopolysiloxane of the present invention preferably has a particular crosslinked structure, for example, a three-dimensional crosslinked structure. An organopolysiloxane having an appropriate crosslinked structure exhibits good stability against organic solvents.

In general, it is difficult to measure number-average molecular weights of three-dimensionally crosslinked polymers. For the sake of convenience, three-dimensionally crosslinked polymers are treated as polymers having an infinite molecular weight.

When the Si ratio of the siloxane compound layer is in the range of 0.6 to 1.0, a siloxane compound can be made present at a high density and homogeneously, membrane defects can be effectively prevented, and the gas separation performance can be further enhanced. Furthermore, it becomes possible to use the membrane under high-pressure, high-temperature, and high-humidity conditions and to further suppress plasticization of the gas separation layer due to impurity components such as toluene.

The Si ratio of the siloxane compound layer in the present invention is preferably 0.7 to 1.0, more preferably 0.75 to 1.0, still more preferably 0.8 to 1.0, and particularly preferably 0.85 to 1.0.

The organopolysiloxane compound layer in the present invention preferably has a structure in which organopolysiloxane compounds are linked to each other through a linking group selected from *—O-M-O—*, *—S-M-S—*, *—NR$^a$C(=O)—*, *—NR$^b$C(=O)NR$^b$—*, *—O—CH$_2$—O—*, *—S—CH$_2$CH$_2$—*, *—OC(=O)O—*, *—CH(OH)CH$_2$OCO—*, *—CH(OH)CH$_2$O—*, *—CH(OH)CH$_2$S—*, *—CH(OH)CH$_2$NR$^c$—*, *—CH(CH$_2$OH)CH$_2$OCO—*, *—CH(CH$_2$OH)CH$_2$O—*, *—CH(CH$_2$OH)CH$_2$S—*, *—CH(CH$_2$OH)CH$_2$NR$^c$—*, *—CH$_2$CH$_2$—*, *—C(=O)O$^-$N$^+$(R$^d$)$_3$—*, *—SO$_3$—N$^+$(R$^e$)$_3$—*, and *—PO$_3$H$^-$N$^+$(R$^f$)$_3$—*.

In the formulae, M represents a divalent to tetravalent metal atom; R$^a$, R$^b$, R$^c$, R$^d$, R$^e$, and R$^f$ each independently represent a hydrogen atom or an alkyl group; and the symbol * represents a linking site.

Examples of the metal atom M include metal atoms selected from aluminum (Al), iron (Fe), beryllium (Be), gallium (Ga), vanadium (V), indium (In), titanium (Ti), zirconium (Zr), copper (Cu), cobalt (Co), nickel (Ni), zinc (Zn), calcium (Ca), magnesium (Mg), yttrium (Y), scandium (Sc), chromium (Cr), manganese (Mn), molybdenum (Mo), and boron (B). Of these, a metal atom selected from Zr, Fe, Zn, Al, Ga, and B is preferable, a metal atom selected from Al and B is more preferable, and Al is still more preferable.

The alkyl groups for R$^a$, R$^b$, R$^c$, R$^d$, R$^e$, and R$^f$ are preferably alkyl groups having 1 to 20 carbon atoms, more preferably alkyl groups having 1 to 10 carbon atoms, still more preferably alkyl groups having 1 to 7 carbon atoms, and particularly preferably alkyl groups having 1 to 4 carbon atoms. These alkyl groups may be linear or branched, and are more preferably linear. Specific preferred examples of the alkyl groups include alkyl groups cited in Group Z of substituents described below.

When the siloxane compound layer has a structure in which siloxane compounds are linked to each other through the above linking group, the Si ratio of the siloxane compound layer can be more easily increased to the range specified in the present invention.

Reactions in which siloxane compounds are linked to each other through the linking group will be described below.

*—O-M-O—*

The linking group *—O-M-O—* can be formed by, for example, a ligand exchange reaction between a siloxane compound having a group having —OH (active hydrogen-containing group), such as a hydroxy group, a carboxy group, or a sulfo group and a metal complex (crosslinking agent) represented by Formula (B) below.

(B)

In the formula, M has the same definition as the above metal atom M, and the preferred form of M is also the same as that of the metal atom M; L represents an alkoxy group, an aryloxy group, an acetylacetonato group, an acyloxy group, a hydroxy group, or a halogen atom; and q represents an integer of 2 to 4.

The alkoxy group for L is preferably an alkoxy group having 1 to 10 carbon atoms, more preferably an alkoxy group having 1 to 4 carbon atoms, and still more preferably an alkoxy group having 1 to 3 carbon atoms. Specific examples of the alkoxy group for L include methoxy, ethoxy, tert-butoxy, and isopropoxy.

The aryloxy group for L is preferably an aryloxy group having 6 to 10 carbon atoms, more preferably an aryloxy group having 6 to 8 carbon atoms, and still more preferably an aryloxy group having 6 to 7 carbon atoms. Specific examples of the aryloxy group for L include phenoxy, 4-methoxyphenoxy, and naphthoxy.

The acyloxy group for L is preferably an acyloxy group having 2 to 10 carbon atoms, more preferably an acyloxy group having 2 to 6 carbon atoms, and still more preferably an acyloxy group having 2 to 4 carbon atoms. Specific examples of the acyloxy group for L include acetoxy, propanoyloxy, pivaloyloxy, and acetyloxy.

Examples of the halogen atom for L include, but are not particularly limited to, a fluorine atom, a chlorine atom, a bromine atom, and an iodine atom. Of these, a chlorine atom is preferred.

The metal complex represented by Formula (B) is preferably soluble in an organic solvent used in a coating solution for forming the siloxane compound layer. More specifically, the degree of solubility of the metal complex represented by Formula (B) in 100 g of tetrahydrofuran at 25° C. is preferably 0.01 to 10 g, and more preferably 0.1 to 1.0 g. When the metal complex represented by Formula (B) is soluble in the organic solvent, a more homogeneous metal-crosslinked siloxane compound layer can be formed.

Specific preferred examples of the metal complex represented by Formula (B) include metal complexes selected from aluminum acetylacetonate, gallium acetylacetonate, indium acetylacetonate, zirconium acetylacetonate, cobalt acetylacetonate, calcium acetylacetonate, nickel acetylacetonate, zinc acetylacetonate, magnesium acetylacetonate, ferric chloride, copper(II) acetate, aluminum isopropoxide, titanium isopropoxide, boric acid, and boron trifluoride-diethyl ether complex.

An example of the ligand exchange reaction is shown below. The example shown below illustrates a case where the siloxane compound has a hydroxy group. In the case where the siloxane compound has another active hydrogen-containing group such as a carboxy group or a sulfo group, a similar ligand exchange reaction proceeds to form the linking group represented by *—O-M-O—*.

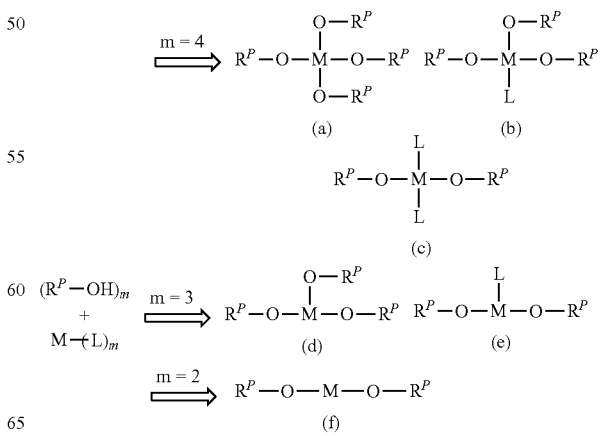

In the formulae, $R^P$ represents a siloxane compound residue (that is, $R^P$—OH represents a siloxane compound having a hydroxy group).

When M is a tetravalent metal atom (m=4), at most four $R^P$—OH can usually coordinate to one M (the form of (a) above). In the present invention, when M is a tetravalent metal atom, all of the form in which two $R^P$—OH coordinate (the form of (c) above), the form in which three $R^P$—OH coordinate (the form of (b) above), and the form in which four $R^P$—OH coordinate (the form of (a) above) are considered to be included in the form having the linking group represented by *—O-M-O—*.

Although not shown in the above formulae, when the siloxane compound $R^P$—OH is represented by $R^{P1}$—$(OH)_h$ (where $R^{P1}$ represents a siloxane compound residue and h represents an integer of 2 or more, that is, in the case of a form having two or more hydroxy groups in one molecule), two or more OH present in one molecule of $R^{P1}$—$(OH)_h$ may coordinate to one M. This form is also considered to be included in the form having the linking group represented by *—O-M-O—*.

When M is a trivalent metal atom (in =3), at most three $R^P$—OH can usually coordinate to one M (the form of (d) above). In the present invention, when M is a trivalent metal atom, both the form in which two $R^P$—OH coordinate (the form of (e) above) and the form in which three $R^P$—OH coordinate (the form of (d) above) are considered to be included in the form having the linking group represented by *—O-M-O—*.

Although not shown in the above formulae, when the siloxane compound $R^P$—OH is represented by $R^{P1}$—$(OH)_h$ (where $R^{P1}$ represents a siloxane compound residue and h represents an integer of 2 or more, that is, in the case of a form having two or more hydroxy groups in one molecule), two or more OH present in one molecule of $R^{P1}$—$(OH)_h$ may coordinate to one M. This form is also considered to be included in the form having the linking group represented by *—O-M-O—*.

When M is a divalent metal atom (m=2), the form of (f) above is the form having the linking group represented by *—O-M-O—* and specified in the present invention.

Although not shown in the above formula, when the siloxane compound $R^P$—OH is represented by $R^{P1}$—$(OH)_h$ (where $R^{P1}$ represents a siloxane compound residue and h represents an integer of 2 or more, that is, in the case of a form having two or more hydroxy groups in one molecule), two or more OH present in one molecule of $R^{P1}$—$(OH)_h$ may coordinate to one M. This form is also considered to be included in the form having the linking group represented by *—O-M-O—*.

*—S-M-S—*

The linking structure *—S-M-S—* can be formed by, for example, a ligand exchange reaction between a siloxane compound having a thiol group and a metal complex represented by Formula (B) above. This reaction includes a reaction form in which $R^P$—OH in the above-described reaction for forming *—O-M-O—* is replaced by $R^P$—SH. Since —SH is also an active hydrogen-containing group, the ligand exchange reaction can be performed in the same manner as described above.

*—$NR^aC(=O)$—*

The linking group *—$NR^aC(=O)$—* can be formed by, for example, allowing a siloxane compound having a carboxy group and a siloxane compound having an amino group to react with each other in the presence of a dehydration condensing agent (for example, a carbodiimide compound). This reaction can be represented by the following formula.

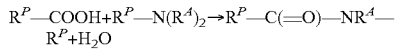

In the formula, $R^P$ represents a siloxane compound residue. Of the two $R^A$ linked to one N on the left side, one $R^A$ is a hydrogen atom and the other $R^A$ is a hydrogen atom or an alkyl group (that is, $R^A$ on the right side is a hydrogen atom or an alkyl group).

Alternatively, the above linking group can be formed by allowing a siloxane compound having a carboxy group and a compound having two or more amino groups and functioning as a crosslinking agent to react with each other. Alternatively, the above linking group can be formed by allowing a siloxane compound having an amino group and a compound having two or more carboxy groups and functioning as a crosslinking agent to react with each other.

*—$NR^bC(=O)NR^b$—*

The linking group *—$NR^bC(=O)NR^b$—* can be formed by, for example, allowing a siloxane compound having an amino group and a chloroformate functioning as a crosslinking agent to react with each other. This reaction can be represented by the following formula.

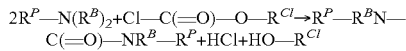

In the formula, $R^P$ represents a siloxane compound residue, and $R^{Cl}$ represents an alcohol residue of a chloroformate. Of the two $R^B$ linked to one N on the left side, one $R^B$ is a hydrogen atom and the other $R^B$ is a hydrogen atom or an alkyl group (that is, each $R^B$ on the right side is a hydrogen atom or an alkyl group).

*—O—$CH_2$—O—*

The linking group *—O—$CH_2$—O—* can be formed by, for example, allowing a siloxane compound having a hydroxy group and formaldehyde functioning as a crosslinking agent to react with each other. This reaction can be represented by the following formula.

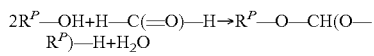

In the formula, $R^P$ represents a siloxane compound residue.

*—S—$CH_2CH_2$—*

The linking group *—S—$CH_2CH_2$—* can be formed by, for example, allowing a siloxane compound having a thiol group and a siloxane compound having a vinyl group to react with each other. This reaction can be represented by the following formula.

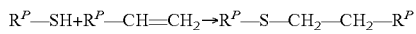

In the formula, $R^P$ represents a siloxane compound residue.

Alternatively, the above linking group can be formed by allowing a siloxane compound having a thiol group and a compound having two or more vinyl groups and functioning as a crosslinking agent to react with each other. Alternatively, the above linking group can be formed by allowing a siloxane compound having a vinyl group and a compound having two or more thiol groups and functioning as a crosslinking agent to react with each other.

*—OC(=O)O—*

The linking group *—OC(=O)O—* can be formed by, for example, allowing a siloxane compound having a hydroxy group and a chloroformate functioning as a crosslinking agent to react with each other. This reaction can be represented by the following formula.

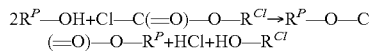

In the formula, $R^P$ represents a siloxane compound residue, and $R^{Cl}$ represents an alcohol residue of a chloroformate.

*—C(=O)O⁻N⁺($R^d$)₃—*

The linking group *—C(=O)O⁻N⁺($R^d$)₃—* can be formed by, for example, allowing a siloxane compound having a carboxy group and a siloxane compound having an amino group to react with each other. This reaction can be represented by the following formula.

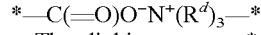

In the formula, $R^P$ represents a siloxane compound residue, and $R^D$ represents a hydrogen atom or an alkyl group.

Alternatively, the above linking structure can be formed by allowing a siloxane compound having a carboxy group and a compound having two or more amino groups and functioning as a crosslinking agent to react with each other. Alternatively, the above linking group can be formed by allowing a siloxane compound having an amino group and a compound having two or more carboxy groups and functioning as a crosslinking agent to react with each other.

*—SO₃⁻N⁺($R^e$)₃—*

The linking group *—SO₃O⁻N⁺($R^e$)₃—* can be formed by, for example, allowing a siloxane compound having a sulfo group and a siloxane compound having an amino group to react with each other. This reaction can be represented by the following formula.

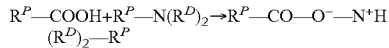

In the formula, $R^P$ represents a siloxane compound residue, and $R^E$ represents a hydrogen atom or an alkyl group.

Alternatively, the above linking group can be formed by allowing a siloxane compound having a sulfo group and a compound having two or more amino groups and functioning as a crosslinking agent to react with each other. Alternatively, the above linking group can be formed by allowing a siloxane compound having an amino group and a compound having two or more sulfo groups and functioning as a crosslinking agent to react with each other.

*—PO₃H⁻N⁺($R^f$)₃—*

The linking structure *—PO₃H⁻N⁺($R^f$)₃—* can be formed by, for example, allowing a siloxane compound having a phosphonic acid group and a siloxane compound having an amino group to react with each other. This reaction can be represented by the following formula.

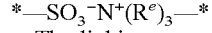

In the formula, $R^P$ represents a siloxane compound residue, and $R^F$ represents a hydrogen atom or an alkyl group.

Alternatively, the above linking group can be formed by allowing a siloxane compound having a phosphonic acid group and a compound having two or more amino groups and functioning as a crosslinking agent to react with each other. Alternatively, the above linking group can be formed by allowing a siloxane compound having an amino group and a compound having two or more phosphonic acid groups and functioning as a crosslinking agent to react with each other.

*—CH(OH)CH₂OCO—*

The linking group *—CH(OH)CH₂OCO—* can be formed by, for example, allowing a siloxane compound having an epoxy group and a siloxane compound having a carboxy group to react with each other.

Alternatively, the above linking group can be formed by allowing a siloxane compound having an epoxy group and a compound having two or more carboxy groups and functioning as a crosslinking agent to react with each other. Alternatively, the above linking group can be formed by allowing a siloxane compound having a carboxy group and a compound having two or more epoxy groups and functioning as a crosslinking agent to react with each other.

*—CH(OH)CH₂O—*

The linking group *—CH(OH)CH₂O—* can be formed by, for example, allowing a siloxane compound having an epoxy group and a siloxane compound having a hydroxy group to react with each other.

Alternatively, the above linking group can be formed by allowing a siloxane compound having an epoxy group and a compound having two or more hydroxy groups and functioning as a crosslinking agent to react with each other. Alternatively, the above linking group can be formed by allowing a siloxane compound having a hydroxy group and a compound having two or more epoxy groups and functioning as a crosslinking agent to react with each other.

*—CH(OH)CH₂S—*

The linking group *—CH(OH)CH₂S—* can be formed by, for example, allowing a siloxane compound having an epoxy group and a siloxane compound having a thiol group to react with each other.

Alternatively, the above linking group can be formed by allowing a siloxane compound having an epoxy group and a compound having two or more thiol groups and functioning as a crosslinking agent to react with each other. Alternatively, the above linking group can be formed by allowing a siloxane compound having a thiol group and a compound having two or more epoxy groups and functioning as a crosslinking agent to react with each other.

*—CH(OH)CH₂N$R^c$—*

The linking group *—CH(OH)CH₂N$R^c$—* can be formed by, for example, allowing a siloxane compound having an epoxy group and a siloxane compound having an amino group to react with each other.

Alternatively, the above linking group can be formed by allowing a siloxane compound having an epoxy group and a compound having two or more amino groups and functioning as a crosslinking agent to react with each other. Alternatively, the above linking group can be formed by allowing a siloxane compound having an amino group and a compound having two or more epoxy groups and functioning as a crosslinking agent to react with each other.

*—CH(CH₂OH)CH₂OCO—*

The linking group *—CH(CH₂OH)CH₂OCO—* can be formed by changing the epoxy group in the formation of the linking group *—CH(OH)CH₂OCO—* to an oxetanyl group.

*—CH(CH₂OH)CH₂O—*

The linking group *—CH(CH₂OH)CH₂O—* can be formed by changing the epoxy group in the formation of the linking group *—CH(OH)CH₂O—* to an oxetanyl group.

*—CH(CH₂OH)CH₂S—*

The linking group *—CH(CH₂OH)CH₂S—* can be formed by changing the epoxy group in the formation of the linking group *—CH(OH)CH₂S—* to an oxetanyl group.

*—CH(CH$_2$OH)CH$_2$NR$^c$—*

The linking group *—CH(CH$_2$OH)CH$_2$NR$^c$—* can be formed by changing the epoxy group in the formation of the linking group *—CH(OH)CH$_2$NR$^c$—* to an oxetanyl group.

*—CH$_2$CH$_2$—*

The linking group *—CH$_2$CH$_2$—* can be formed by, for example, a polymerization reaction of siloxane compounds having a vinyl group (such as a (meth)acryloyl group).

In the present invention, the linking structure through *—CH$_2$CH$_2$—* does not include the linking structure through *—S—CH$_2$CH$_2$—*.

The siloxane compound layer may have one of the above linking structures or two or more of the above linking structures.

In the siloxane compound layer in the present invention, from the viewpoint of reactivity for forming the linking structure and chemical stability of the linking structure, the linking structure of siloxane compounds is preferably at least one linking structure through a linking group selected from *—O-M-O—*, *—S-M-S—*, *—O—CH$_2$—O—*, *—S—CH$_2$CH$_2$—*, *—OC(=O)O—*, *—CH$_2$CH$_2$—*, or *—C(=O)O$^-$N$^+$(R$^d$)$_3$—* described above, more preferably at least one linking structure through a linking group selected from *—O-M-O—*, *—S-M-S—*, *—O—CH$_2$—O—*, *—S—CH$_2$CH$_2$—*, or *—CH$_2$CH$_2$—*, and still more preferably at least one linking structure through a linking group selected from *—O-M-O—* or *—CH$_2$CH$_2$—*. Even still more preferably, the siloxane compound layer includes both the linking structure through *—O-M-O—* and the linking structure through *—CH$_2$CH$_2$—*.

The siloxane compounds (siloxane compounds before the formation of the linking structure through the linking group) used as raw materials of the siloxane compound layer are not particularly limited as long as the siloxane compounds have functional groups that provide the above linking structure. Specific preferred examples of the polysiloxane compounds include at least one selected from methacrylate-modified polydialkylsiloxanes, methacrylate-modified polydiarylsiloxanes, methacrylate-modified polyalkylarylsiloxanes, thiol-modified polydialkylsiloxanes, thiol-modified polydiarylsiloxanes, thiol-modified polyalkylarylsiloxanes, hydroxy-modified polydialkylsiloxanes, hydroxy-modified polydiarylsiloxanes, hydroxy-modified polyalkylarylsiloxanes, amine-modified polydialkylsiloxanes, amine-modified polydiarylsiloxanes, amine-modified polyalkylarylsiloxanes, vinyl-modified polydialkylsiloxanes, vinyl-modified polydiarylsiloxanes, vinyl-modified polyalkylarylsiloxanes, carboxy-modified polydialkylsiloxanes, carboxy-modified polydiarylsiloxanes, carboxy-modified polyalkylarylsiloxanes, hydrosilyl-modified polydialkylsiloxanes, hydrosilyl-modified polydiarylsiloxanes, hydrosilyl-modified polyalkylarylsiloxanes, epoxy-modified polydialkylsiloxanes, epoxy-modified polydiarylsiloxanes, epoxy-modified polyalkylarylsiloxanes, oxetanyl-modified polydialkylsiloxanes, oxetanyl-modified polydiarylsiloxanes, or oxetanyl-modified polyalkylarylsiloxanes.

In the above polysiloxane compounds cited as examples, the site modified with each functional group may be a terminal or a side chain. The polysiloxane compounds preferably have two or more modified sites per molecule. Each of the functional groups introduced by the modification may further have a substituent.

The quantitative ratio of the alkyl group to the aryl group in each of the "polyalkylarylsiloxanes" is not particularly limited. Specifically, each of the "polyalkylarylsiloxanes" may have a dialkylsiloxane structure or a diarylsiloxane structure in the structure thereof.

In the siloxane compounds cited as examples, the number of carbon atoms of the alkyl group is preferably 1 to 10, more preferably 1 to 5, and still more preferably 1 to 3. The alkyl group is even still more preferably methyl. In the siloxane compounds cited as examples, the number of carbon atoms of the aryl group is preferably 6 to 20, more preferably 6 to 15, and still more preferably 6 to 12. The aryl group is even still more preferably phenyl.

The siloxane compound layer in the present invention preferably has at least one structure selected from (a) or (b).

(a) A structure having a structure represented by General formula (1) and a structure represented by General formula (2) or General formula (3)

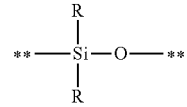

General formula (1)

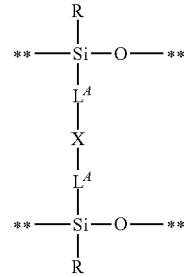

General formula (2)

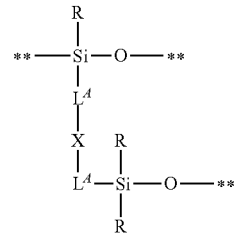

General formula (3)

(b) A structure represented by General formula (4)

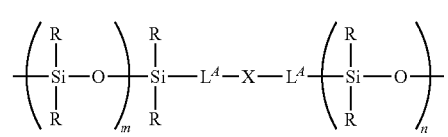

General formula (4)

In the formulae, R represents an alkyl group or an aryl group; L$^A$ represents a single bond or a divalent linking group; X represents a linking group selected from *—O-M$^1$-O—*, *—S-M$^1$-S—*, *—O—CH$_2$—O—*, *—S—CH$_2$CH$_2$—*, *—OC(=O)O—*, *—CH$_2$CH$_2$—*, and *—C(=O)O$^-$N$^+$(R$^d$)$_3$—* where M$^1$ represents Zr, Fe, Zn, B, Al, or Ga and R$^d$ represents a hydrogen atom or an alkyl group; and m and n are each an integer of 2 or more (preferably an integer of 2 to 300). The symbol "*" represents a linking site. The symbol "" represents a linking site in a siloxane bond (that is, in General formulae (1) to (3), when an O atom is adjacent to the symbol , the symbol ** represents a site linking to a Si atom. In General formulae (1) to (3), when a Si atom is adjacent to the symbol , the symbol  represents a site linking to an O atom.)

The terminal structure of General formula (4) is preferably a group selected from a hydrogen atom, a mercapto group, an amino group, a vinyl group, a carboxy group, an oxetane group, a sulfonic acid group, and a phosphonic acid group.

When R is an alkyl group, the alkyl group is preferably an alkyl group having 1 to 10 carbon atoms, more preferably an alkyl group having 1 to 5 carbon atoms, still more preferably an alkyl group having 1 to 3 carbon atoms, and particularly preferably methyl.

When R is an aryl group, the number of carbon atoms of the aryl group is preferably 6 to 20, more preferably 6 to 15, and still more preferably 6 to 12. The aryl group is even still more preferably a phenyl group.

When $L^A$ is a divalent linking group, the divalent linking group is preferably an alkylene group (preferably an alkylene group having 1 to 10 carbon atoms and more preferably an alkylene group having 1 to 5 carbon atoms), an arylene group (preferably an arylene group having 6 to 20 carbon atoms, more preferably an arylene group having 6 to 15 carbon atoms, and still more preferably a phenylene group), or —Si(R)$_2$—O— (where R has the same definition as in General formula (2), and the preferred form of R is also the same as that in General formula (2)). The "O" in —Si(R)$_2$—O— is linked to Si in General formula (2) or (3).

The structure of (a) above preferably has a repeating unit represented by Formula (5) besides the structure represented by any of General formulae (1) to (3).

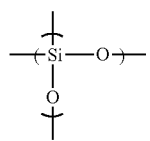

Formula (5)

It is also preferable that the repeating unit represented by Formula (5) be present in the siloxane compound layer in the form of a structure in which the repeating units represented by Formula (5) are linked to each other through a siloxane bond.

In the siloxane compound layer in the present invention, a content ratio of the repeating unit represented by Formula (5) is preferably 0.01 to 0.55, more preferably 0.05 to 0.40, and still more preferably 0.10 to 0.35.

The content ratio of the repeating unit represented by Formula (5) is measured by the method described in Examples below.

In the gas separation membrane of the present invention, the siloxane compound layer preferably contains 10 to 5,000 ppm of an organic solvent on a mass basis. When the siloxane compound layer contains an organic solvent in the above-mentioned range, the gas separation performance can be stabilized from the early stage of the first use of the gas separation membrane (that is, it is possible to reduce the time necessary from the first use to stabilization of gas permeability and gas separation selectivity at a predetermined level).

The content of the organic solvent present in the siloxane compound layer is preferably 10 to 1,000 ppm and more preferably 30 to 500 ppm on a mass basis from the viewpoint of further stabilizing the gas separation performance of the gas separation membrane from the early stage of the first use.

The organic solvent contained in the siloxane compound layer is not particularly limited and is usually an organic solvent used for preparing a coating solution by dissolving a siloxane compound in the formation of the siloxane compound layer. Preferred examples of the organic solvent include organic solvents selected from pentane, hexane, heptane, octane, nonane, decane, benzene, toluene, xylene, methyl ethyl ketone, methyl isobutyl ketone, N-methylpyrrolidone, N-ethylpyrrolidone, dimethyl sulfoxide, dimethylacetamide, dimethylformamide, methylene chloride, tetrahydrofuran, dioxane, and 1,3-dioxolane. Organic solvents selected from hexane, heptane, toluene, and tetrahydrofuran are more preferable.

In the present invention, the thickness of the siloxane compound layer is preferably 10 to 600 nm, and more preferably 10 to 300 nm.

Group Z of Substituents

Group Z of substituents includes alkyl groups (the number of carbon atoms of each of the alkyl groups is preferably 1 to 30, more preferably 1 to 20, and particularly preferably 1 to 10, and examples thereof include methyl, ethyl, isopropyl, tert-butyl, n-octyl, n-decyl, and n-hexadecyl); cycloalkyl groups (the number of carbon atoms of each of the cycloalkyl groups is preferably 3 to 30, more preferably 3 to 20, and particularly preferably 3 to 10, and examples thereof include cyclopropyl, cyclopentyl, and cyclohexyl); alkenyl groups (the number of carbon atoms of each of the alkenyl groups is preferably 2 to 30, more preferably 2 to 20, and particularly preferably 2 to 10, and examples thereof include vinyl, allyl, 2-butenyl, and 3-pentenyl); alkynyl groups (the number of carbon atoms of each of the alkynyl groups is preferably 2 to 30, more preferably 2 to 20, and particularly preferably 2 to 10, and examples thereof include propargyl and 3-pentynyl); aryl groups (the number of carbon atoms of each of the aryl groups is preferably 6 to 30, more preferably 6 to 20, and particularly preferably 6 to 12, and examples thereof include phenyl, p-methylphenyl, naphthyl, and anthranyl); amino groups (examples thereof include an amino group, alkylamino groups, arylamino groups, and heterocyclic amino groups, the number of carbon atoms of each of the amino groups is preferably 0 to 30, more preferably 0 to 20, and particularly preferably 0 to 10, and specific examples thereof include amino, methylamino, dimethylamino, diethylamino, dibenzylamino, diphenylamino, and ditolylamino); alkoxy groups (the number of carbon atoms of each of the alkoxy groups is preferably 1 to 30, more preferably 1 to 20, and particularly preferably 1 to 10, and examples thereof include methoxy, ethoxy, butoxy, and 2-ethylhexyloxy); aryloxy groups (the number of carbon atoms of each of the aryloxy groups is preferably 6 to 30, more preferably 6 to 20, and particularly preferably 6 to 12, and examples thereof include phenyloxy, 1-naphthyloxy, and 2-naphthyloxy); heterocyclic oxy groups (the number of carbon atoms of each of the heterocyclic oxy groups is preferably 1 to 30, more preferably 1 to 20, and particularly preferably 1 to 12, and examples thereof include pyridyloxy, pyrazyloxy, pyrimidyloxy, and quinolyloxy);

acyl groups (the number of carbon atoms of each of the acyl groups is preferably 1 to 30, more preferably 1 to 20, and particularly preferably 1 to 12, and examples thereof include acetyl, benzoyl, formyl, and pivaloyl); alkoxycarbonyl groups (the number of carbon atoms of each of the alkoxycarbonyl groups is preferably 2 to 30, more preferably 2 to 20, and particularly preferably 2 to 12, and examples thereof include methoxycarbonyl and ethoxycarbonyl); aryloxycarbonyl groups (the number of carbon atoms of each of the aryloxycarbonyl groups is preferably 7 to 30, more preferably 7 to 20, and particularly preferably 7 to 12, and examples thereof include phenyloxycarbonyl); acyloxy groups (the number of carbon atoms of each of the acyloxy groups is preferably 2 to 30, more preferably 2 to 20, and particularly preferably 2 to 10, and examples thereof include acetoxy and benzoyloxy); acylamino groups (the number of carbon atoms of each of the acylamino groups is preferably 2 to 30, more preferably 2 to 20, and particularly preferably 2 to 10, and examples thereof include acetylamino and benzoylamino);

alkoxycarbonylamino groups (the number of carbon atoms of each of the alkoxycarbonylamino groups is preferably 2 to 30, more preferably 2 to 20, and particularly preferably 2 to 12, and examples thereof include methoxycarbonylamino); aryloxycarbonylamino groups (the number of carbon atoms of each of the aryloxycarbonylamino groups is preferably 7 to 30, more preferably 7 to 20, and particularly preferably 7 to 12, and examples thereof include phenyloxycarbonylamino); sulfonylamino groups (the number of carbon atoms of each of the sulfonylamino groups is preferably 1 to 30, more preferably 1 to 20, and particularly preferably 1 to 12, and examples thereof include methanesulfonylamino and benzenesulfonylamino); sulfamoyl groups (the number of carbon atoms of each of the sulfamoyl groups is preferably 0 to 30, more preferably 0 to 20, and particularly preferably 0 to 12, and examples thereof include sulfamoyl, methylsulfamoyl, dimethylsulfamoyl, and phenylsulfamoyl);

carbamoyl groups (the number of carbon atoms of each of the carbamoyl groups is preferably 1 to 30, more preferably 1 to 20, and particularly preferably 1 to 12, and examples thereof include carbamoyl, methylcarbamoyl, diethylcarbamoyl, and phenylcarbamoyl); alkylthio groups (the number of carbon atoms of each of the alkylthio groups is preferably 1 to 30, more preferably 1 to 20, and particularly preferably 1 to 12, and examples thereof include methylthio and ethylthio); arylthio groups (the number of carbon atoms of each of the arylthio groups is preferably 6 to 30, more preferably 6 to 20, and particularly preferably 6 to 12, and examples thereof include phenylthio); heterocyclic thio groups (the number of carbon atoms of each of the heterocyclic thio groups is preferably 1 to 30, more preferably 1 to 20, and particularly preferably 1 to 12, and examples thereof include pyridylthio, 2-benzimidazolylthio, 2-benzoxazolylthio, and 2-benzothiazolylthio);

sulfonyl groups (the number of carbon atoms of each of the sulfonyl groups is preferably 1 to 30, more preferably 1 to 20, and particularly preferably 1 to 12, and examples thereof include mesyl and tosyl); sulfinyl groups (the number of carbon atoms of each of the sulfinyl groups is preferably 1 to 30, more preferably 1 to 20, and particularly preferably 1 to 12, and examples thereof include methanesulfinyl and benzenesulfinyl); ureido groups (the number of carbon atoms of each of the ureido groups is preferably 1 to 30, more preferably 1 to 20, and particularly preferably 1 to 12, and examples thereof include ureido, methylureido, and phenylureido); phosphoric amide groups (the number of carbon atoms of each of the phosphoric amide groups is preferably 1 to 30, more preferably 1 to 20, and particularly preferably 1 to 12, and examples thereof include diethyl phosphoric amide and phenyl phosphoric amide); a hydroxy group; a mercapto group; halogen atoms (such as a fluorine atom, a chlorine atom, a bromine atom, and an iodine atom, and a fluorine atom is more preferable);

a cyano group; a sulfo group; a carboxyl group; an oxo group; a nitro group; a hydroxamic acid group; a sulfino group; a hydrazino group; an imino group; heterocyclic groups (3- to 7-membered ring heterocyclic groups are preferable, the heterocycle may be aromatic or non-aromatic, examples of the heteroatom contained in the heterocycle include a nitrogen atom, an oxygen atom, and a sulfur atom, the number of carbon atoms of each of the heterocyclic groups is preferably 0 to 30 and more preferably 1 to 12, and specific examples thereof include imidazolyl, pyridyl, quinolyl, furyl, thienyl, piperidyl, morpholino, benzoxazolyl, benzimidazolyl, benzothiazolyl, carbazolyl, and azepinyl); silyl groups (the number of carbon atoms of each of the silyl groups is preferably 3 to 40, more preferably 3 to 30, and particularly preferably 3 to 24, and examples thereof include trimethylsilyl and triphenylsilyl); and silyloxy groups (the number of carbon atoms of each of the silyloxy groups is preferably 3 to 40, more preferably 3 to 30, and particularly preferably 3 to 24, and examples thereof include trimethylsilyloxy and triphenylsilyloxy). These substituents may be further substituted with any one or more substituents selected from Group Z of substituents described above.

In the present invention, when one structural site has a plurality of substituents, these substituents may be linked to each other to form a ring or may be fused with part or the whole of the structural site to form an aromatic ring or an unsaturated heterocyclic ring.

Gas Separation Membrane

Structures of the gas separation membrane of the present invention will be described.

Composite Gas Separation Membrane

In a composite gas separation membrane which is a preferred embodiment of a gas separation membrane of the present invention (hereinafter, may be referred to as "composite membrane of the present invention"), a gas separation layer containing the cellulose resin described above is formed on the upper side of a gas-permeable support layer (porous layer). As described later, this composite membrane can be formed by applying (the term "applying" (or "coating") used herein includes a manner of deposition on a surface by immersion), to at least a surface of a porous support, a coating solution (dope) containing a component (cellulose resin) which forms the gas separation layer. Furthermore, in the composite membrane of the present invention, a siloxane compound layer is formed on the upper side of the gas separation layer so as to be in contact with the gas separation layer.

Figure 2:
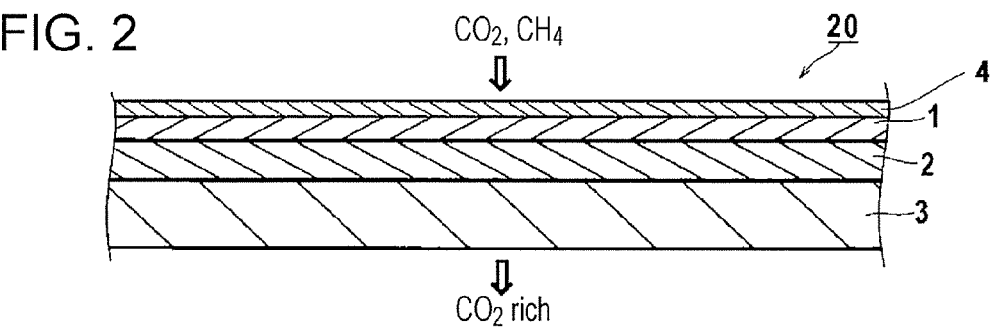
FIG. 2 is a schematic sectional view illustrating a gas separation membrane according to another preferred embodiment (composite membrane) of the present invention.
Figure 3:
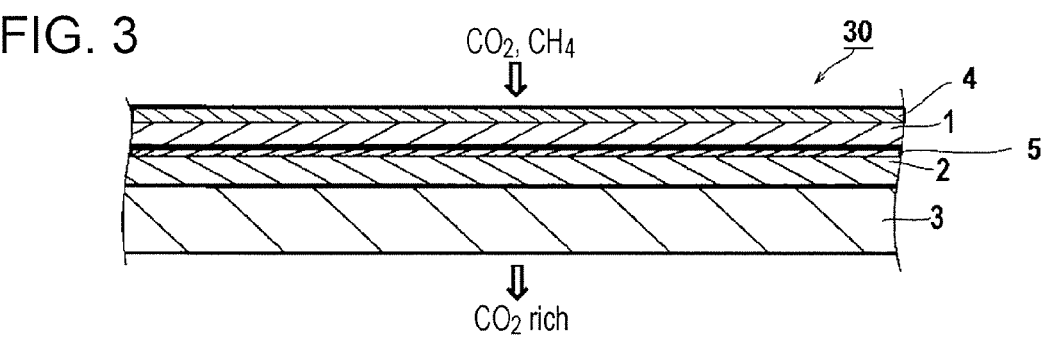
FIG. 3 is a schematic sectional view illustrating a gas separation membrane according to still another preferred embodiment (composite membrane) of the present invention.

FIG. 1 is a schematic vertical sectional view illustrating a composite gas separation membrane 10 according to a preferred embodiment of the present invention. Reference numeral 1 indicates a gas separation layer, reference numeral 2 indicates a porous layer 2, and reference numeral 4 indicates a siloxane compound layer. FIG. 2 is a schematic sectional view illustrating a composite gas separation membrane 20 according to another preferred embodiment of the present invention. In this embodiment, in addition to the gas separation layer 1, the porous layer 2, and the siloxane compound layer 4, a nonwoven fabric layer 3 is provided as an additional support layer. FIG. 3 is a schematic sectional view illustrating a composite gas separation membrane 30 according to still another preferred embodiment of the present invention. In this embodiment, in addition to the gas separation layer 1, the porous layer 2, the siloxane compound layer 4, and the nonwoven fabric layer 3, a smooth layer 5 is provided as an underlayer of the gas separation layer 1 so as to be in contact with the gas separation layer 1.

Herein, the term "on the upper side of a support layer" means that another layer may be disposed between a support layer and a gas separation layer. Regarding the expression of the upper and lower sides, the side to which target gas to be separated is supplied is defined as the "upper side", and the side from which the separated gas is discharged is defined as the "lower side" unless otherwise stated.

Herein, the term "having gas permeability" means that when carbon dioxide is supplied to a support layer (a membrane consisting of a support layer) at a total pressure on the gas supply side of 4 MPa at a temperature of 40° C., the permeation rate of the carbon dioxide is $1 \times 10^{-5}$ cm$^3$ (STP)/cm$^2$·sec·cmHg (10 GPU) or more. The gas permeability is preferably 50 GPU or more, and more preferably 100 GPU or more.

In the composite membrane of the present invention, a gas separation layer may be formed and disposed on a surface or in an inner surface of a porous layer. A composite membrane can be easily obtained by forming a gas separation layer at least on a surface of a porous layer. Formation of a gas separation layer at least on a surface of a porous layer can provide a composite membrane having an advantage that high separation selectivity, high gas permeability, and mechanical strength are combined. The thickness of the separation layer is preferably as small as possible under conditions in which high gas permeability is provided while mechanical strength and separation selectivity are maintained.

In the composite membrane of the present invention, the thickness of the gas separation layer is not particularly limited, but is preferably 0.01 to 5.0 µm, more preferably 0.05 to 2.0 µm, and still more preferably 0.05 to 1.0 µm.

The porous layer is not particularly limited as long as the purpose of providing mechanical strength and high gas permeability is satisfied. The porous layer may be formed of an organic material or an inorganic material. The porous layer is preferably a porous membrane formed of an organic polymer. The thickness of the porous layer is 1 to 3,000 µm, preferably 5 to 500 µm, and more preferably 5 to 150 m. Regarding the pore structure of the porous layer, the average pore size is usually 10 m or less, preferably 0.5 µm or less, and more preferably 0.2 m or less. The porosity is preferably 20% to 90%, and more preferably 30% to 80%.

The porous layer preferably has a molecular weight cut-off of 100,000 or less. Furthermore, the gas permeance of the porous layer is preferably $3 \times 10^{-5}$ cm$^3$ (STP)/cm$^2$·sec·cmHg (30 GPU) or more, more preferably 100 GPU or more, and still more preferably 200 GPU or more in terms of the permeation rate of carbon dioxide at 40° C. and 4 MPa.

Examples of the material of the porous layer include known polymers such as polyolefin resins, e.g., polyethylene and polypropylene; fluorine-containing resins, e.g., polytetrafluoroethylene, polyvinyl fluoride, and polyvinylidene fluoride; and other resins, e.g., polystyrene, cellulose acetate, polyurethane, polyacrylonitrile, polyphenylene oxide, polysulfone, polyethersulfone, polyimide, and polyaramid.

The porous layer may have any shape such as a flat-plate shape, a spiral shape, a tubular shape, or a hollow fiber shape.

The composite membrane of the present invention preferably has a support for providing mechanical strength, the support being disposed on the lower side of the porous layer that forms a gas separation layer. Examples of the support include woven fabrics, nonwoven fabrics, and nets. From the viewpoint of membrane formability and the cost, a nonwoven fabric is suitably used. As the nonwoven fabric, fibers formed of polyester, polypropylene, polyacrylonitrile, polyethylene, polyamide, or the like may be used alone or in combination of two or more thereof. The nonwoven fabric can be produced by, for example, papermaking main fibers and binder fibers that are uniformly dispersed in water with a circular net, a long net, or the like, and drying the fibers with a dryer. Furthermore, for the purpose of, for example, removing fuzz or improving mechanical properties, it is also preferable to perform a thermal pressing process by interposing the nonwoven fabric between two rolls.

In the production of a composite membrane of the present invention, the gas separation layer is provided by, preferably, applying a coating solution containing at least a cellulose resin to a porous layer or a smooth layer, which will be described later, and drying the coating solution to form the gas separation layer.

The content of the cellulose resin in the coating solution is not particularly limited, but is preferably 0.1% to 30% by mass, and more preferably 0.5% to 10% by mass. When the content of the cellulose resin is excessively low, the coating solution easily permeates through the lower layer (porous support) in the formation of a membrane on the porous support. Accordingly, there is a concern that defects are likely to be generated in a surface layer that contributes to separation. When the content of the cellulose resin is excessively high, in the formation of a membrane on the porous support, pores are filled with the cellulose resin at a high concentration, which may decrease permeability. The gas separation membrane of the present invention can be appropriately produced by adjusting the molecular weight, the structure, the composition, and the solution viscosity of the polymer of the separation layer.

As the organic solvent serving as a medium of the coating solution for forming the gas separation layer, it is preferable to select a suitable organic solvent that does not erode a support to which the coating solution is to be applied. Examples of the organic solvent include hydrocarbon organic solvents such as n-hexane and n-heptane; ester organic solvents such as methyl acetate, ethyl acetate, and butyl acetate; lower alcohols such as methanol, ethanol, n-propanol, isopropanol, n-butanol, isobutanol, and tert-butanol; aliphatic ketones such as acetone, methyl ethyl ketone, methyl isobutyl ketone, diacetone alcohol, cyclopentanone, and cyclohexanone; ether organic solvents such as ethylene glycol, diethylene glycol, triethylene glycol, glycerin, propylene glycol, ethylene glycol monomethyl or monoethyl ether, propylene glycol methyl ether, dipropylene glycol methyl ether, tripropylene glycol methyl ether, ethylene glycol phenyl ether, propylene glycol phenyl ether, diethylene glycol monomethyl or monoethyl ether, diethylene glycol monobutyl ether, triethylene glycol monomethyl or monoethyl ether, dibutyl butyl ether, tetrahydrofuran, methyl cyclopentyl ether, and dioxane; N-methylpyrrolidone; 2-pyrrolidone; dimethylformamide; dimethylimidazolidinone; dimethyl sulfoxide; and dimethylacetamide. These organic solvents are suitably selected within a range that does not adversely affect the support through erosion or the like. Esters (preferably, butyl acetate), alcohols (preferably, methanol, ethanol, isopropanol, and isobutanol), aliphatic ketones (preferably, methyl ethyl ketone, methyl isobutyl ketone, diacetone alcohol, cyclopentanone, and cyclohexanone), and ethers (ethylene glycol, diethylene glycol monomethyl ether, and methyl cyclopentyl ether) are preferable. Aliphatic ketones, alcohols, and ethers are more preferable. These organic solvents may be used alone or in combination of two or more thereof.

In the composite membrane of the present invention, a siloxane compound layer is disposed on the upper side of the gas separation layer so as to be in contact with the gas separation layer. The siloxane compound layer can be preferably formed by applying, onto the gas separation layer, a coating solution containing at least a siloxane compound (at least one siloxane compound having a reactive group for forming any of the linking groups described above), performing light irradiation, heat treatment, or the like optionally in the presence of a catalyst, a condensing agent, and a polymerization initiator to link siloxane compounds through a desired linking group.

The content of the siloxane compound in the coating solution is not particularly limited, but is preferably 0.1% to 30% by mass, and more preferably 0.5% to 10% by mass.

A medium of the coating solution for forming the siloxane compound layer is preferably a solvent selected from pentane, hexane, heptane, octane, nonane, decane, benzene, toluene, xylene, N-methylpyrrolidone, N-ethylpyrrolidone, dimethyl sulfoxide, dimethylacetamide, dimethylformamide, methylene chloride, dioxane, and 1,3-dioxolane.

In the composite membrane of the present invention, the thickness of the siloxane compound layer is preferably 0.01 to 5 μm, and more preferably 0.05 to 1 μm from the viewpoint of smoothness and gas permeability.

The gas permeance of the siloxane compound layer at 40° C. and 4 MPa is preferably 100 GPU or more, more preferably 300 GPU or more, and still more preferably 1,000 GPU or more in terms of the permeation rate of carbon dioxide.

Another Layer

In the composite membrane of the present invention, a smooth layer is preferably provided between the porous layer and the gas separation layer, the smooth layer serving as an underlayer in contact with the gas separation layer. When the smooth layer is provided, it is possible to smooth the unevenness on the surface of the porous layer and thus a reduction in the thickness of the gas separation layer is easily realized. This smooth layer is preferably a siloxane compound layer. The preferred form of the siloxane compound layer is the same as that of the siloxane compound layer described above.

Asymmetric Gas Separation Membrane

Figure 4:
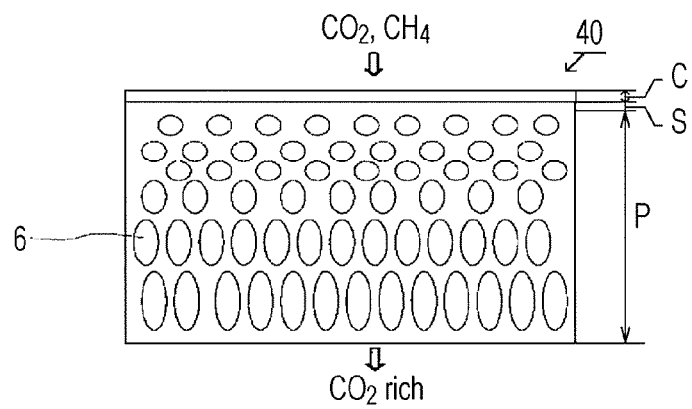
FIG. 4 is a schematic view illustrating a gas separation membrane according to still another preferred embodiment (asymmetric membrane) of the present invention.

Another preferred embodiment of the gas separation membrane of the present invention is a form of an asymmetric membrane. FIG. 4 is a schematic view illustrating a preferred embodiment of an asymmetric gas separation membrane of the present invention. An asymmetric gas separation membrane 40 has, on the gas supply side, a thin skin layer (S, hereinafter, may be referred to as "dense layer" or "gas separation layer") that contributes to gas separation and a siloxane compound layer (C, hereinafter, may be referred to as "protective layer") formed on the skin layer. A portion other than the skin layer is a thick porous layer (P). This porous layer functions as a support. The porous layer (P) has pores penetrating from an end on the upper side thereof to an end on the lower side thereof. Unlike the skin layer (S), the porous layer (P) does not have a gas separation capability.

The asymmetric gas separation membrane of the present invention (hereinafter, may be referred to as "asymmetric membrane of the present invention") can be formed by a phase inversion process using a solution (dope solution) containing a cellulose resin. The phase inversion process is a known process for forming a membrane by bringing a dope solution into contact with a coagulating liquid while causing a phase inversion, and a so-called dry-wet process is suitably used in the present invention. The dry-wet process includes evaporating a solution on a surface of a dope solution that is formed to have a membrane shape, and subsequently immersing the resulting membrane in a coagulating liquid (a solvent which is compatible with a solvent of the dope solution and in which the cellulose resin is insoluble) to form a dense layer and to simultaneously form a porous layer by forming fine pores using a phase-separation phenomenon that occurs at this time. This process was suggested by Loeb, Sourirajan, et al. (for example, the specification of U.S. Pat. No. 3,133,132).

Through the step of evaporating the solution on the surface of the dope solution, the solvent is volatilized from the surface of the coating solution, and moisture in the air is absorbed. As a result, the surface becomes solidified easily, and it is possible to stabilize the thickness of the dense layer (skin layer) formed when the resulting membrane is brought into contact with the coagulating liquid.

A medium used in the preparation of the dope solution is preferably a solvent miscible with the coagulating liquid so as to cause phase inversion. More preferably, as the medium of the dope solution, an aprotic polar organic solvent selected from N-methylpyrrolidone, N-ethylpyrrolidone, γ-butyrolactone, dimethyl sulfoxide, dimethylacetamide, dimethylformamide, methylene chloride, tetrahydrofuran, dioxane, and 1,3-dioxolane is at least used. It is also preferable that a solvent such as a ketone, an alcohol, acetonitrile, or water be further mixed with any of the solvents mentioned above to prepare the medium of the dope solution.

The coagulating liquid is preferably formed of a mixture of water and a protic polar solvent (preferably, an alcohol).

Examples of the support to which the dope solution is applied include porous membranes such as nanofiltration membranes, ultrafiltration membranes, microfiltration membranes, nonwoven fabrics, and woven fabrics. Of these, nonwoven fabrics are preferable. The forms of preferred nonwoven fabrics are the same as those in the description of the composite membranes. When a dope solution is applied onto a porous membrane such as a nonwoven fabric, part of the dope solution permeates through pores of the porous membrane, and a phase-separation phenomenon occurs in this state. Therefore, the resulting gas separation membrane containing a cellulose resin may be integrated with the porous membrane such as a nonwoven fabric to form a gas separation membrane. That is, it is also preferable that the porous layer include a porous support and fine pores formed by curing the dope solution. Herein, this state is denoted by the phrase "an asymmetric membrane is supported by a porous membrane". Particularly preferable is a gas separation membrane in which an asymmetric membrane is supported by using a nonwoven fabric which is a preferred porous membrane.

The thickness of the asymmetric membrane of the present invention is preferably 10 to 200 μm (when the asymmetric membrane is supported by a porous membrane such as a nonwoven fabric, the term "thickness" refers to a thickness including the thickness of the porous membrane). The thickness of the surface layer (i.e., gas separation layer) that is referred to as a dense layer or a skin layer and that contributes to gas separation is not particularly limited. However, from the viewpoint of providing practical gas permeability, the thickness of the surface layer is preferably 0.01 to 5.0 μm, more preferably 0.05 to 2.0 μm, and still more preferably 0.05 to 1.0 μm.

The asymmetric gas separation membrane of the present invention may be a flat membrane or a hollow-fiber membrane. Asymmetric hollow-fiber membranes can be produced by a dry-wet spinning process. The dry-wet spinning process is a process for producing an asymmetric hollow-fiber membrane by applying a dry-wet process to a dope solution which is ejected from a spinning nozzle to have a desired hollow fiber shape. More specifically, the dry-wet spinning process is a process for producing an asymmetric membrane by ejecting a dope solution from a nozzle to have a desired hollow fiber shape, allowing the dope solution to pass through air or a nitrogen gas atmosphere immediately after the ejection, and then immersing the resulting dope solution in a coagulating liquid which does not substantially dissolve a cellulose resin and which is compatible with a solvent of the dope solution to form an asymmetric structure, then drying the dope solution, and further performing heat treatment as needed.

The solution viscosity of the dope solution to be ejected from a nozzle is 2 to 1,700 Pa·s, preferably 10 to 1,500 Pa·s, and particularly preferably 20 to 1,000 Pa·s at an ejection temperature (for example, 10° C.) because the shape after ejection, such as a hollow fiber shape, can be stably obtained. It is preferable that immersion in a coagulating liquid be performed by immersing the ejected dope solution in a primary coagulating liquid to be coagulated to such an extent that the shape of the membrane such as a hollow fiber can be maintained, then winding the resulting membrane around a guide roll, and subsequently immersing the membrane in a secondary coagulating liquid so as to sufficiently coagulate the whole membrane. It is effective that the coagulated membrane is dried after the coagulating liquid is substituted with a solvent such as a hydrocarbon.

In the asymmetric membrane of the present invention, the siloxane compound layer described above is disposed on the upper side of the skin layer (gas separation layer) so as to be in contact with the skin layer. The formation of the siloxane compound layer can be performed as in the formation of the siloxane compound in the composite membrane of the present invention.

In the gas separation membranes (composite membranes and asymmetric membranes) of the present invention, the content of the cellulose resin in the gas separation layer is not particularly limited as long as a desired gas separation performance is obtained. From the viewpoint of improving the gas separation performance, the content of the cellulose resin in the gas separation layer is preferably 20% by mass or more, more preferably 40% by mass or more, still more preferably 60% by mass or more, and even still more preferably 70% by mass or more. The content of the cellulose resin in the gas separation layer may be 100% by mass but is usually 99% by mass or less.

Use and Characteristics of Gas Separation Membrane

The gas separation membranes (composite membranes and asymmetric membranes) of the present invention can be suitably used for gas separation-recovery and gas separation-purification. For example, it is possible to obtain gas separation membranes that are capable of efficiently separating specific gas from a gas mixture containing gas such as hydrogen, helium, carbon monoxide, carbon dioxide, hydrogen sulfide, oxygen, nitrogen, ammonia, sulfur oxides, nitrogen oxides, hydrocarbons, e.g., methane and ethane, unsaturated hydrocarbons, e.g., propylene, and perfluoro compounds, e.g., tetrafluoroethane. In particular, it is preferable to obtain a gas separation membrane that selectively separates carbon dioxide from a gas mixture containing carbon dioxide and a hydrocarbon (methane).

When the gas to be subjected to a separation treatment is mixed gas of carbon dioxide and methane, the permeation rate of carbon dioxide at 40° C. and 5 MPa is preferably more than 20 GPU, more preferably more than 30 GPU, and still more preferably 50 to 500 GPU. The ratio of the permeation rate of carbon dioxide to the permeation rate of methane ($R_{CO2}/R_{CH4}$, may be referred to as separation selectivity) is preferably 15 or more, more preferably 20 or more, still more preferably 23 or more, and particularly preferably 25 to 50 where $R_{CO2}$ represents the permeation rate of carbon dioxide and $R_{CH4}$ represents the permeation rate of methane.

Note that 1 GPU is $1\times10^{-6}$ cm$^3$ (STP)/cm$^2$·sec·cmHg.

Other Components

In order to adjust membrane physical properties, various polymer compounds may also be added to the gas separation layer of the gas separation membrane of the present invention. Examples of the polymer compounds that can be used include acrylic polymers, polyurethane resins, polyamide resins, polyester resins, epoxy resins, phenolic resins, polycarbonate resins, polyvinyl butyral resins, polyvinyl formal resins, shellac, vinyl resins, acrylic resins, rubber resins, waxes, and other natural resins. These polymer compounds may be used in combination of two or more thereof.

In order to adjust liquid physical properties, for example, a nonionic surfactant, a cationic surfactant, or an organofluorine compound may also be added.

Specific examples of the surfactants include anionic surfactants such as alkyl benzene sulfonates, alkyl naphthalene sulfonates, higher fatty acid salts, sulfonates of higher fatty acid esters, sulfuric acid ester salts of higher alcohol ethers, sulfonates of higher alcohol ethers, alkyl carboxylates of higher alkyl sulfonamides, and alkyl phosphates; nonionic surfactants such as polyoxyethylene alkyl ethers, polyoxyethylene alkyl phenyl ethers, polyoxyethylene fatty acid esters, sorbitan fatty acid esters, ethylene oxide adducts of acetylene glycol, ethylene oxide adducts of glycerin, and polyoxyethylene sorbitan fatty acid esters; amphoteric surfactants such as alkyl betaines and amide betaines; silicon-based surfactants; and fluorine-based surfactants. The surfactant can be suitably selected from known surfactants including the above specific examples and derivatives thereof.

A high-molecular-weight dispersant may also be contained. Specific examples of the high-molecular-weight dispersant include polyvinylpyrrolidone, polyvinyl alcohol, polyvinyl methyl ether, polyethylene oxide, polyethylene glycol, polypropylene glycol, and polyacrylamide. Of these, polyvinylpyrrolidone is preferably used.

The conditions for forming the gas separation membrane of the present invention are not particularly limited. The temperature is preferably −30° C. to 100° C., more preferably −10° C. to 80° C., and particularly preferably 5° C. to 50° C.

In the present invention, during the formation of the membrane, gas such as air or oxygen may be allowed to coexist. However, it is desirable that the membrane be formed under an inert gas atmosphere.

Method for Separating Gas Mixture

A gas separation method of the present invention is a method that includes selectively allowing permeation of specific gas from mixed gas containing two or more types of gas by using the gas separation membrane of the present invention to perform separation. In particular, the gas separation method of the present invention is preferably a method that includes selectively allowing permeation of carbon dioxide from mixed gas containing carbon dioxide and methane. The pressure of gas during the gas separation is preferably 0.5 to 10 MPa, more preferably 1 to 10 MPa, and still more preferably 2 to 7 MPa.

The temperature of gas when the gas separation method of the present invention is performed is preferably −30° C. to 90° C., and more preferably 15° C. to 70° C. In the mixed gas containing carbon dioxide and methane gas, the mixing ratio of carbon dioxide to methane gas is not particularly limited. The mixing ratio is preferably carbon dioxide:methane gas=1:99 to 99:1 (volume ratio) and more preferably carbon dioxide:methane gas=5:95 to 90:10 (volume ratio).

Gas Separation Module and Gas Separation Apparatus

A gas separation module can be prepared by using the gas separation membrane of the present invention. Examples of the module include a spiral-type module, a hollow fiber-type module, a pleated module, a tubular module, and a plate & frame-type module.

Furthermore, a gas separation apparatus having means for performing separation and recovery of gas or performing separation and purification of gas can be obtained by using the gas separation membrane or the gas separation module of the present invention. The gas separation membrane of the present invention may be applied to a gas separation-recovery apparatus for a membrane/absorption hybrid method in which a membrane is used in combination with an absorption liquid, as described in, for example, Japanese Unexamined Patent Application Publication No. 2007-297605.

EXAMPLES

The present invention will be described in more detail with reference to Examples. The present invention is not limited to these Examples.

[Example 1] Preparation of Asymmetric Membrane

To 0.5 g of cellulose acetate (trade name: L-70, available from Daicel Corporation, acetylation degree 0.55, where the term "acetylation degree" refers to a weight percentage of bonded acetic acid per unit weight) serving as a cellulose resin, a mixture of 2.5 g of methyl ethyl ketone, 2.5 g of N,N-dimethylformamide (DMF), and 0.6 g of n-butanol was added to dissolve the cellulose acetate. The resulting solution was filtered with a PTFE microfiltration membrane having a pore size of 5.0 μm to prepare a dope solution.

A polyester nonwoven fabric (available from Awa Paper Mfg. Co., Ltd., thickness: 95 μm) was placed on a clean glass plate (10 cm in length×10 cm in width×1 mm in thickness, hereinafter the same), and the dope solution was applied onto the nonwoven fabric at room temperature (20° C.). The resulting glass plate was allowed to stand for 30 seconds and then immersed in a primary coagulating liquid (0° C., 75% by mass methanol aqueous solution) for one hour. Subsequently, the glass plate was further immersed in a secondary coagulating liquid (0° C., 75% by mass methanol aqueous solution) for one hour to prepare an asymmetric membrane. The prepared asymmetric membrane was washed with methanol, and the methanol was then replaced by isooctane. Furthermore, the asymmetric membrane was heated at 50° C. for eight hours and then heated at 110° C. for six hours to evaporate and dry the isooctane. In this manner, a crosslinked cellulose asymmetric membrane in which the thickness of a dense gas separation layer was 0.1 μm or less and a total thickness of a polymer layer was 40 m was obtained. This asymmetric membrane had a thickness of 95 m, which included the thickness of the nonwoven fabric.

Formation of Siloxane Compound Layer

Preparation of Radiation-Curable Polymer Having Polysiloxane Structure

A both-terminal methacrylate-modified polydimethylsiloxane X-22-164E (Compound 1, available from Shin-Etsu Chemical Co., Ltd.) (39 g) and a both-terminal thiol-modified polydimethylsiloxane X-22-167B (Compound 2, available from Shin-Etsu Chemical Co., Ltd.) (10 g) were placed in a 300 mL three-necked flask, and 50 g of n-heptane was further added to the flask to dissolve the polydimethylsiloxanes. The resulting solution was maintained at 50° C. for five hours to prepare a solution of a radiation-curable polymer having a polysiloxane structure.

Preparation of Radiation-Curable Composition

The radiation-curable polymer solution (2.5 g) was cooled to 20° C. and diluted by adding 95 g of n-heptane. Irgacure 184 (available from BASF) (0.01 g) as a photopolymerization initiator was added to the resulting solution to prepare a radiation-curable composition.

Formation of Siloxane Compound Layer

The radiation-curable composition was applied onto the gas separation layer of the asymmetric membrane by spin coating. Subsequently, the resulting asymmetric membrane was irradiated with UV (Light Hammer 10, D bulb, available from Fusion UV Systems, Inc.) under UV treatment conditions of a UV intensity of 24 kW/m and a treatment time of 10 seconds. Subsequently, the asymmetric membrane after UV irradiation was dried at 70° C. for two hours to form a siloxane compound layer. As a result, an asymmetric membrane (gas separation membrane) that had a gas separation layer and a siloxane compound layer having a thickness of about 0.5 μm and disposed on the gas separation layer was prepared. This siloxane compound layer has a structure in which siloxane compounds are linked to each other through —S—CH$_2$CH$_2$— and a structure in which siloxane compounds are linked to each other through —CH$_2$CH$_2$—.

[Examples 2 to 24] Preparation of Asymmetric Membranes

Asymmetric membranes (gas separation membranes) of Examples 2 to 24 were prepared as in Example 1 except that cellulose resins and siloxane compounds described in Tables 1-1 to 1-4 were used instead of the cellulose resin (cellulose acetate) and the siloxane compounds (Compound 1 and Compound 2) used in Example 1, and crosslinking agents (metal complexes) described in Tables 1-1 to 1-4 were added to radiation-curable compositions used in the formation of siloxane compound layers.

Instead of the N,N-dimethylformamide used as a medium of the dope solution for forming an asymmetric membrane in Example 1, N-methyl-2-pyrrolidone was used in Examples 4 to 14 and Example 16, dimethyl sulfoxide was used in Examples 15 and 20, N-ethyl-2-pyrrolidone was used in Example 18, γ-butyrolactone was used in Example 19, dimethylacetamide was used in Example 21, methylene chloride was used in Example 22, dioxane was used in Example 23, and 1,3-dioxolane was used in Example 24.

[Comparative Example 1] Preparation of Asymmetric Membrane

A cellulose acetate asymmetric membrane was prepared with reference to the method described in U.S. Pat. No.

6,368,382. Specifically, a mixed solution of 4.7 g of dioxane, 2.0 g of acetone, 1.2 g of methanol, 0.2 g of lactic acid, and 0.3 g of n-decane was added to 0.8 g of cellulose acetate (trade name: CA-398-3, available from Eastman Chemical Company) to dissolve the cellulose acetate. The resulting solution was then filtered with a PTFE microfiltration membrane having a pore size of 5.0 m to prepare a dope solution. A polyester nonwoven fabric (available from Awa Paper Mfg. Co., Ltd., thickness: 95 µm) was placed on a clean glass plate, and the dope solution was further applied onto the nonwoven fabric at room temperature (20° C.). The resulting glass plate was allowed to stand for 30 seconds and then immersed in a primary coagulating liquid (2° C., water) for 10 minutes. The glass plate was further immersed in a secondary coagulating liquid (80° C. to 90° C., water) for 15 minutes to prepare an asymmetric membrane. The prepared asymmetric membrane was washed with methanol, and the methanol was then further evaporated and dried at 60° C. to 70° C. In this manner, an asymmetric membrane (gas separation membrane) in which the thickness of a dense gas separation layer was 0.1 µm or less and a total thickness of a polymer layer was 40 µm was obtained. This asymmetric membrane had a thickness of 110 µm, which included the thickness of the nonwoven fabric.

[Comparative Example 2] Preparation of Asymmetric Membrane

An asymmetric membrane (gas separation membrane) of Comparative Example 2 was prepared as in Comparative Example 1 except that the cellulose resin described in Table 1-4 was used instead of the cellulose resin used in Comparative Example 1.

[Comparative Example 3] Preparation of Asymmetric Membrane

An epoxysilicone UV-curable polymer was prepared with reference to the method described in U.S. Pat. No. 6,368,382. Specifically, 4 g of UV9315 (available from Momentive Performance Materials Inc.) was placed in a 200 mL three-necked flask, and 96 g of a mixture of n-hexane and n-heptane with a composition ratio of n-hexane:n-heptane=1:3 was added to the flask to dissolve the UV9315 to prepare a silicone polymer. Subsequently, 3 g of UV9380C (available from Momentive Performance Materials Inc.) as a photopolymnerization initiator was added to the resulting solution of the silicone polymer to prepare a radiation-curable composition. Furthermore, the radiation-curable composition was applied, by spin coating, onto a gas separation layer of an asymmetric membrane prepared as in Comparative Example 1. Subsequently, the resulting asymmetric membrane was irradiated with UV (Light Hammer 10, D bulb, available from Fusion UV Systems, Inc.) under UV treatment conditions of a UV intensity of 24 kW/m and a treatment time of 10 seconds. Subsequently, the asymmetric membrane after UV irradiation was dried at 70° C. for two hours to form a siloxane compound layer. As a result, an asymmetric membrane (gas separation membrane) that had a gas separation layer and a siloxane compound layer having a thickness of 0.5 µm and disposed on a surface of the gas separation layer was obtained.

[Comparative Example 4] Preparation of Asymmetric Membrane

An asymmetric membrane of Comparative Example 4 was prepared as in Comparative Example 3 except that the cellulose resin described in Table 1-4 was used instead of the cellulose resin used in Comparative Example 3.

[Comparative Examples 5 and 6] Preparation of Asymmetric Membranes

Asymmetric membranes of Comparative Examples 5 and 6 were prepared as in Comparative Example 3 except that the cellulose resin described in Table 1-4 was used instead of the cellulose resin used in Comparative Example 3, and N,N-dimethylformamide was used instead of dioxane.

In Tables 1-1 to 1-4 below, the abbreviation "acac" represents an acetylacetonato group, and the abbreviation "OiPr" represents an isopropoxy group.

Cellulose resins having a weight-average molecular weight in the range of 30,000 to 300,000 were used in the Examples.

TABLE 1-1

|  | Cellulose resin used for forming asymmetric membrane | Siloxane compound or crosslinking agent used for siloxane compound layer | |
|---|---|---|---|
|  |  | Compound 1 | Compound 2 |
| Example 1 | Cellulose acetate L-70 (available from Daicel Corporation) | Both-terminal methacrylate-modified polydimethylsiloxane X-22-164E (available from Shin-Etsu Chemical Co., Ltd.) | Both-terminal thiol-modified polydimethylsiloxane X-22-167B (available from Shin-Etsu Chemical Co., Ltd.) |
| Example 2 | Cellulose acetate L-70 (available from Daicel Corporation) | Both-terminal methacrylate-modified polydimethylsiloxane X-22-164E (available from Shin-Etsu Chemical Co., Ltd.) | Both-terminal thiol-modified polydimethylsiloxane X-22-167B (available from Shin-Etsu Chemical Co., Ltd.) |
| Example 3 | Cellulose acetate L-70 (available from Daicel Corporation) | Both-terminal methacrylate-modified polydimethylsiloxane X-22-164E (available from Shin-Etsu Chemical Co., Ltd.) | — |
| Example 4 | Cellulose acetate LT-55 (available from Daicel Corporation) | Both-terminal hydroxy-modified polydimethylsiloxane X-22-170DX (available from Shin-Etsu Chemical Co., Ltd.) | 1,3,5-Trioxane T0505 (available from Tokyo Chemical Industry Co., Ltd.) |
| Example 5 | Cellulose acetate L-50 (available from Daicel Corporation) | Both-terminal methacrylate-modified polydimethylsiloxane X-22-164E (available from Shin-Etsu Chemical Co., Ltd.) | Both-terminal thiol-modified polydimethylsiloxane X-22-167B (available from Shin-Etsu Chemical Co., Ltd.) |
| Example 6 | Cellulose acetate L-30 (available from Daicel Corporation) | Both-terminal thiol-modified polydimethylsiloxane X-22-167B (available from Shin-Etsu Chemical Co., Ltd.) | — |

TABLE 1-1-continued

| | | | |
|---|---|---|---|
| Example 7 | Cellulose acetate propionate 341541 (available from Sigma-Aldrich) | Both-terminal amine-modified polydimethylsiloxane KF-8008 (available from Shin-Etsu Chemical Co., Ltd.) | Both-terminal carboxy-modified polydimethylsiloxane X-22-162C (available from Shin-Etsu Chemical Co., Ltd.) |
| Example 8 | Cellulose acetate propionate 341541 (available from Sigma-Aldrich) | Both-terminal vinyl-modified polydimethylsiloxane 433012 (Sigma-Aldrich) | Both-terminal thiol-modified polydimethylsiloxane X-22-167B (available from Shin-Etsu Chemical Co., Ltd.) |

| | Metal complex (Crosslinking agent) | | |
|---|---|---|---|
| | Compound | Amount added relative to total 100 parts by mass of siloxane compounds (parts by mass) | Linking group linking siloxane compounds to each other |
| Example 1 | None | — | —S—$CH_2CH_2$— —$CH_2CH_2$— |
| Example 2 | Al(acac)$_3$ | 3 | —S—$CH_2CH_2$— —$CH_2CH_2$— —S—Al—S— |
| Example 3 | — | — | —$CH_2CH_2$— |
| Example 4 | Al(acac)$_3$ | 15 | —O—$CH_2O$— —O—Al—O— |
| Example 5 | FeCl$_3$ | 5 | —S—$CH_2CH_2$— —$CH_2CH_2$— —S—Fe—S— |
| Example 6 | Ga(acac)$_3$ | 1 | —S—Ga—S— |
| Example 7 | In(acac)$_3$ | 1 | —O—In—O— —C(=O)O$^-$N$^+$H$_3$— |
| Example 8 | Ti(OiPr)$_4$ | 0.5 | —S—$CH_2CH_2$— —$CH_2CH_2$— —S—Ti—S— |

TABLE 1-2

| | Cellulose resin used for forming asymmetric membrane | Siloxane compound or crosslinking agent used for siloxane compound layer | |
|---|---|---|---|
| | | Compound 1 | Compound 2 |
| Example 9 | Cellulose acetate phthalate 038-01702 (available from Wako Pure Chemical Industries, Ltd.) | Both-terminal vinyl-modified polydimethylsiloxane 433012 (Sigma-Aldrich) | Both-terminal hydrosilyl-modified polydimethylsiloxane 482145 (Sigma-Aldrich) |
| Example 10 | Cellulose acetate phthalate 038-01702 (available from Wako Pure Chemical Industries, Ltd.) | Both-terminal amine-modified polydimethylsiloxane KF-8008 (available from Shin-Etsu Chemical Co., Ltd.) | Both-terminal acid anhydride-modified polydimethylsiloxane DMS-Z21 (available from Gelest, Inc.) |
| Example 11 | Cellulose acetate phthalate 038-01702 (available from Wako Pure Chemical Industries, Ltd.) | Vinyl-modified siloxane compound VQM-146 (available from Gelest, Inc.) | Both-terminal hydrosilyl-modified polydimethylsiloxane 482145 (Sigma-Aldrich) |
| Example 12 | Cellulose acetate phthalate 038-01702 (available from Wako Pure Chemical Industries, Ltd.) | Both-terminal amine-modified polydimethylsiloxane KF-8008 (available from Shin-Etsu Chemical Co., Ltd.) | Methyl chloroformate C0180 (available from Tokyo Chemical Industry Co., Ltd.) |
| Example 13 | Cellulose acetate phthalate 038-01702 (available from Wako Pure Chemical Industries, Ltd.) | Both-terminal hydroxy-modified polydimethylsiloxane X-22-170DX (available from Shin-Etsu Chemical Co., Ltd.) | Methyl chloroformate C0180 (available from Tokyo Chemical Industry Co., Ltd.) |
| Example 14 | Cellulose acetate phthalate 038-01702 (available from Wako Pure Chemical Industries, Ltd.) | Both-terminal carboxy-modified polydimethylsiloxane X-22-162C (available from Shin-Etsu Chemical Co., Ltd.) | — |
| Example 15 | Cellulose acetate phthalate 038-01702 (available from Wako Pure Chemical Industries, Ltd.) | Both-terminal methacrylate-modified polydimethylsiloxane X-22-164E (available from Shin-Etsu Chemical Co., Ltd.) | Both-terminal thiol-modified polydimethylsiloxane X-22-167B (available from Shin-Etsu Chemical Co., Ltd.) |

TABLE 1-2-continued

| | | Metal complex (Crosslinking agent) | | |
|---|---|---|---|---|
| | | Compound | Amount added relative to total 100 parts by mass of siloxane compounds (parts by mass) | Linking group linking siloxane compounds to each other |
| | Example 9 | — | — | —CH$_2$CH$_2$— |
| | Example 10 | — | — | —NHC(=O)— |
| | Example 11 | Cu(OAc)$_2$ | 0.5 | —CH$_2$CH$_2$—<br>—O—Cu—O— |
| | Example 12 | Co(acac)$_2$ | 1 | —NHC(=O)NH— |
| | Example 13 | Al(OiPr)$_3$ | 8 | —O(C=O)O—<br>—O—Al—O— |
| | Example 14 | Ni(acac)$_2$ | 0.5 | —O—Ni—O— |
| | Example 15 | Ga(acac)$_3$ | 5 | —S—CH$_2$CH$_2$—<br>—CH$_2$CH$_2$—<br>—S—Ga—S— |

TABLE 1-3

| | Cellulose resin used for forming asymmetric membrane | Siloxane compound or crosslinking agent used for siloxane compound layer | |
|---|---|---|---|
| | | Compound 1 | Compound 2 |
| Example 16 | Cellulose acetate phthalate 038-01702 (available from Wako Pure Chemical Industries, Ltd.) | Vinyl-modified siloxane compound VQM-146 (available from Gelest, Inc.) | Both-terminal hydrosilyl-modified polydimethylsiloxane 482145 (Sigma-Aldrich) |
| Example 17 | Cellulose acetate L-70 (available from Daicel Corporation) | Vinyl-modified siloxane compound VQM-146 (available from Gelest, Inc.) | Side-chain hydrosilyl-modified polydimethylsiloxane 482382 (Sigma-Aldrich) |
| Example 18 | Cellulose acetate L-70 (available from Daicel Corporation) | Vinyl-modified siloxane compound VQM-146 (available from Gelest, Inc.) | Both-terminal hydrosilyl-modified polydimethylsiloxane 482145 (Sigma-Aldrich) |
| Example 19 | Cellulose acetate L-70 (available from Daicel Corporation) | Vinyl-modified siloxane compound VQM-146 (available from Gelest, Inc.) | Both-terminal hydrosilyl-modified polydimethylsiloxane 482145 (Sigma-Aldrich) |
| Example 20 | Cellulose acetate CA-398-3 (available from Eastman Chemical Company) | Vinyl-modified siloxane compound VQM-146 (available from Gelest, Inc.) | Both-terminal hydrosilyl-modified polydimethylsiloxane 482145 (Sigma-Aldrich) |
| Example 21 | Cellulose acetate CA-435-75S (available from Eastman Chemical Company) | Vinyl-modified siloxane compound VQM-146 (available from Gelest, Inc.) | Both-terminal hydrosilyl-modified polydimethylsiloxane 482145 (Sigma-Aldrich) |
| Example 22 | Cellulose acetate L-70 (available from Daicel Corporation) | Vinyl-modified siloxane compound VQM-146 (available from Gelest, Inc.) | Both-terminal hydrosilyl-modified polydimethylsiloxane 482145 (Sigma-Aldrich) |

| | | Metal complex (Crosslinking agent) | | |
|---|---|---|---|---|
| | | Compound | Amount added relative to total 100 parts by mass of siloxane compounds (parts by mass) | Linking group linking siloxane compounds to each other |
| | Example 16 | B(OH)$_3$ | 15 | —CH$_2$CH$_2$—<br>—O—B—O— |
| | Example 17 | Al(acac)$_3$ | 3 | —CH$_2$CH$_2$—<br>—O—Al—O— |
| | Example 18 | Al(acac)$_3$ | 3 | —CH$_2$CH$_2$—<br>—O—Al—O— |
| | Example 19 | Al(acac)$_3$ | 3 | —CH$_2$CH$_2$—<br>—O—Al—O— |
| | Example 20 | Al(acac)$_3$ | 3 | —CH$_2$CH$_2$—<br>—O—Al—O— |
| | Example 21 | Al(acac)$_3$ | 3 | —CH$_2$CH$_2$—<br>—O—Al—O— |
| | Example 22 | Al(acac)$_3$ | 3 | —CH$_2$CH$_2$—<br>—O—Al—O— |

TABLE 1-4

|  | Cellulose resin used for forming asymmetric membrane | Siloxane compound or crosslinking agent used for siloxane compound layer | |
|---|---|---|---|
|  |  | Compound 1 | Compound 2 |
| Example 23 | Cellulose acetate L-70 (available from Daicel Corporation) | Vinyl-modified siloxane compound VQM-146 (available from Gelest, Inc.) | Both-terminal hydrosilyl-modified polydimethylsiloxane 482145 (Sigma-Aldrich) |
| Example 24 | Cellulose acetate LT-70 (available from Daicel Corporation) | Vinyl-modified siloxane compound VQM-146 (available from Gelest, Inc.) | Both-terminal hydrosilyl-modified polydimethylsiloxane 482145 (Sigma-Aldrich) |
| Comparative Example 1 | Cellulose acetate CA-398-3 (available from Eastman Chemical Company) | None | None |
| Comparative Example 2 | Cellulose acetate CA-435-75S (available from Eastman Chemical Company) | None | None |
| Comparative Example 3 | Cellulose acetate CA-398-3 (available from Eastman Chemical Company) | Both-terminal epoxy-modified polydimethylsiloxane UV9315 (available from Momentive Performance Materials Inc.) | None |
| Comparative Example 4 | Cellulose acetate CA-435-75S (available from Eastman Chemical Company) | Both-terminal epoxy-modified polydimethylsiloxane UV9315 (available from Momentive Performance Materials Inc.) | None |
| Comparative Example 5 | Cellulose acetate CA-398-3 (available from Eastman Chemical Company) | Both-terminal epoxy-modified polydimethylsiloxane UV9315 (available from Momentive Performance Materials Inc.) | None |
| Comparative Example 6 | Cellulose acetate CA-435-75S (available from Eastman Chemical Company) | Both-terminal epoxy-modified polydimethylsiloxane UV9315 (available from Momentive Performance Materials Inc.) | None |

|  | Metal complex (Crosslinking agent) | | |
|---|---|---|---|
|  | Compound | Amount added relative to total 100 parts by mass of siloxane compounds (parts by mass) | Linking group linking siloxane compounds to each other |
| Example 23 | Al(acac)$_3$ | 3 | —CH$_2$CH$_2$— —O—Al—O— |
| Example 24 | Al(acac)$_3$ | 3 | —CH$_2$CH$_2$— —O—Al—O— |
| Comparative Example 1 | None |  |  |
| Comparative Example 2 | None |  |  |
| Comparative Example 3 | None |  | —CHOCH$_2$CH(OH)— |
| Comparative Example 4 | None |  | —CHOCH$_2$CH(OH)— |
| Comparative Example 5 | None |  | —CHOCH$_2$CH(OH)— |
| Comparative Example 6 | None |  | —CHOCH$_2$CH(OH)— |

Vinyl-Modified Siloxane Compound VQM-146

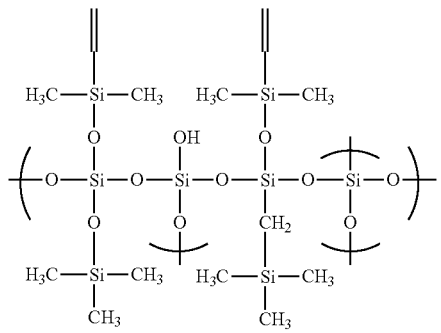

Both-Terminal Epoxy-Modified UV9315

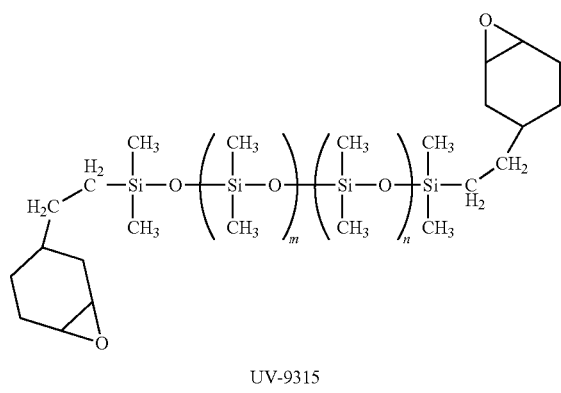

UV-9315

[Test Example 1] Measurement of Content of Organic Solvent

Each of the siloxane compound layers of the gas separation membranes prepared in Examples and Comparative Examples was cut out to have a size of 1 cm×1 cm square. The resulting siloxane compound layer was immersed in 30 mL of chloroform for 24 hours at room temperature to extract the remaining heptane. This extracted liquid was used as a sample for measuring the content of an organic solvent. The content (ppm, on a mass basis) of the organic solvent in the siloxane compound layer was measured by headspace gas chromatography (GC) using the sample. The measurement conditions were as follows.

Measurement Conditions
 Vial keep-warm temperature: 80° C.
 Vial keep-warm time: 30 min.
 Amount of injection: 0.8 mL
 Column: PEG-1500 20% on Shimalite (2.6 mm×3 m)
 Column temperature: 80° C.
 Injection port temperature: 150° C.
 Detection temperature: 150° C.
 Column flow rate: $N_2$ 50 mL/min.
 Detector: FID

[Test Example 2] Measurement of Si Ratio

Each of the gas separation membranes prepared in Examples and Comparative Examples was cut out to have a size of 2.5 cm square. The gas separation membrane was immersed in 500 g of chloroform at 25° C. for 12 hours. Subsequently, the separation membrane was removed and dried under vacuum. A surface of the membrane was then irradiated with X-rays (X-ray fluorescence spectrometry, apparatus: XRF-1700 available from Shimadzu Corporation) to measure the intensity of a peak (2θ=144.6 degrees) of the Si—Kα ray of the X-ray fluorescence. The measured value and a value of the Si—Kα X-ray measured by similarly irradiating the surface of the membrane before the immersion in chloroform with X-rays were substituted for Mathematical expression (I) described above to calculate the Si ratio.

[Test Example 3] Measurement of Content Ratio of Repeating Unit Represented by Formula (5)

Each of the gas separation membranes prepared in Examples and Comparative Examples was cut out to have a size of 2.5 cm square, thus preparing samples for measurement. The samples for measurement were each subjected to X-ray photoelectron spectroscopy (apparatus: Quantera SXM available from ULVAC-PHI, Incorporated) under conditions of an X-ray source of Al-Kα ray (1490 eV, 25 W, 100 μmϕ), a measurement region of 300 μm×300 μm, a pass energy of 55 eV, and a step of 0.05 eV to measure the Si2p (around 98 to 104 eV). Peaks of a T component (103 eV) and a Q component (104 eV) were separated, quantified, and compared. Specifically, a ratio [SA]/([SA]+[ST]) was calculated on the basis of an X-ray fluorescence intensity [SA] of a Si—O bond energy peak of the repeating unit (Q component) represented by Formula (5) and a total intensity [ST] of Si—O bond energy peaks of structures (T component) other than the repeating unit represented by Formula (5). This ratio was defined as the content ratio of the repeating unit represented by Formula (5).

[Test Example 4] Evaluation of Membrane Formability

Fifty samples of each of the gas separation membranes prepared in Examples and Comparative Examples were prepared. The permeance of hydrogen of each of the 50 samples was measured. Samples having a hydrogen permeance of more than $1\times10^6$ mL/m²·24 h·atm were determined as membranes having pinholes (sample errors), and a sample error rate was determined by using a formula given below. The membrane formability was evaluated on the basis of the sample error rate in accordance with evaluation criteria, which are described below.

Sample error rate (%)=100×[the number of sample errors/50]

Evaluation Criteria for Membrane Formability
 AA: Error rate was 2% or less.
 A: Error rate was more than 2% and 5% or less.
 B: Error rate was more than 5%.

[Test Example 5] Evaluation of Gas Separation Performance

The gas separation performance was evaluated as described below by using each of the gas separation membranes prepared in Examples and Comparative Examples.

The gas separation membranes with nonwoven fabrics were each cut in a circular shape having a diameter of 47 mm to prepare permeation test samples. Mixed gas of carbon dioxide ($CO_2$) and methane ($CH_4$) ($CO_2$:$CH_4$=30:70 (volume ratio)) was adjusted so as to have a total pressure on the gas supply side of 4 MPa (partial pressure of $CO_2$: 1.2 MPa), a flow rate of 500 mL/min, and a temperature of 45° C. and supplied from the skin layer side by using a gas permeation analysis apparatus available from GTR Tec Corporation. Gas that had permeated through each of the gas separation membranes was analyzed by gas chromatography. The gas permeabilities of the gas separation membranes were compared to each other by calculating a gas permeation rate as gas permeance. The gas permeance (gas permeation rate) was represented in units of GPU [1 GPU=1×10$^{-6}$ cm$^3$(STP)/cm$^2$·sec·cmHg]. The gas separation selectivity was calculated as a ratio ($R_{CO2}/R_{CH4}$) of the permeation rate $R_{CO2}$ of $CO_2$ to the permeation rate $R_{CH4}$ of $CH_4$ of the gas separation membrane.

[Test Example 6] Evaluation of Folding Endurance

The gas separation membrane of the present invention is often used in the form of a package which is filled with a gas separation membrane and is referred to as a module or an element. When a gas separation membrane is used in the form of a module, the module is filled with the gas separation membrane at a high density in order to ensure a large membrane surface area. In the case of a flat membrane, the membrane fills the module in a state of being folded in a spiral manner.

In view of this, for the asymmetric membranes prepared in Examples and Comparative Examples, an operation of folding at 90 degrees and unfolding to the original state was performed 50 times. Subsequently, the gas permeance was again measured as in Test Example 5. The folding endurance was evaluated on the basis of a change in the permeability of methane gas in accordance with evaluation criteria, which are described below.

Evaluation Criteria for Folding Endurance
  A: Permeance of methane gas hardly changed before and after the folding.
  B: Permeance of methane gas increased obviously after the folding.
  C: Permeance of methane gas increased significantly after the folding.

[Test Example 7] Wet Heat Aging Test

The gas separation membranes prepared in Examples and Comparative Examples were stored under conditions of 80° C. and a relative humidity of 90% (low-temperature constant temperature and humidity chamber, available from Isuzu Seisakusho Co., Ltd., quartz crystal) for 24 hours. The gas separation selectivity was then determined as in Test Example 5. The results are shown in tables below.

[Test Example 8] Toluene Exposure Test

An empty 100 mL beaker was allowed to stand in a glass container which contained a toluene solvent and to which it was possible to attach a lid to cover the toluene solvent. Strips of the gas separation membranes prepared in Examples and Comparative Examples were placed in the beaker, and the glass container was sealed by being covered with the glass lid. Subsequently, the gas separation membranes were stored at 30° C. for two hours. The gas separation selectivity was then determined as in Test Example 5 by using these strips. This toluene exposure test enables the evaluation of resistance to plasticization of gas separation membranes due to impurity components.

Tables 2-1 and 2-2 show the results of Test Examples described above.

TABLE 2-1

| | Content of organic solvent [ppm, on a mass basis] | Si ratio [mass %] | Content ratio of repeating unit of Formula (5) | Membrane formability [Sample error rate (%)] | Folding endurance | $CO_2$ permeance [GPU] | $R_{CO2}/R_{CH4}$ Untreated | After wet heat test | After toluene exposure |
|---|---|---|---|---|---|---|---|---|---|
| Example 1 | 55 | 0.94 | 0 | AA | A | 93 | 45 | 43 | 42 |
| Example 2 | 84 | 0.82 | 0 | A | A | 89 | 41 | 39 | 38 |
| Example 3 | 120 | 0.86 | 0 | AA | A | 97 | 44 | 43 | 42 |
| Example 4 | 214 | 0.79 | 0 | A | A | 82 | 36 | 33 | 31 |
| Example 5 | 45 | 0.67 | 0 | A | A | 82 | 40 | 39 | 39 |
| Example 6 | 34 | 0.83 | 0 | A | A | 81 | 36 | 34 | 35 |
| Example 7 | 56 | 0.70 | 0 | A | A | 84 | 35 | 35 | 34 |
| Example 8 | 70 | 0.72 | 0 | A | B | 77 | 34 | 31 | 29 |
| Example 9 | 105 | 0.80 | 0 | A | A | 81 | 30 | 25 | 24 |
| Example 10 | 92 | 0.60 | 0 | A | A | 89 | 37 | 33 | 30 |
| Example 11 | 59 | 0.72 | 0.1 | A | A | 77 | 39 | 36 | 35 |
| Example 12 | 66 | 0.70 | 0 | A | B | 86 | 32 | 30 | 29 |
| Example 13 | 315 | 0.70 | 0 | A | A | 80 | 37 | 35 | 32 |
| Example 14 | 30 | 0.60 | 0 | A | A | 86 | 28 | 27 | 26 |
| Example 15 | 45 | 0.70 | 0 | A | A | 67 | 35 | 34 | 32 |
| Example 16 | 170 | 0.64 | 0.42 | A | A | 85 | 30 | 28 | 28 |
| Example 17 | 95 | 0.72 | 0.21 | A | A | 75 | 39 | 37 | 33 |
| Example 18 | 150 | 0.85 | 0.07 | AA | A | 94 | 42 | 41 | 40 |

TABLE 2-2

| | Content of organic solvent [ppm, on a mass basis] | Si ratio [mass %] | Content ratio of repeating unit of Formula (5) | Membrane formability [Sample error rate (%)] | Folding endurance | CO$_2$ permeance [GPU] | $R_{CO2}/R_{CHA}$ Untreated | After wet heat test | After toluene exposure |
|---|---|---|---|---|---|---|---|---|---|
| Example 19 | 45 | 0.92 | 0.12 | AA | A | 97 | 43 | 42 | 41 |
| Example 20 | 1020 | 0.88 | 0.11 | AA | A | 94 | 42 | 41 | 41 |
| Example 21 | 140 | 0.76 | 0.15 | A | A | 80 | 39 | 36 | 36 |
| Example 22 | 400 | 0.72 | 0.35 | A | A | 83 | 38 | 36 | 35 |
| Example 23 | 125 | 0.76 | 0.11 | A | A | 86 | 39 | 37 | 38 |
| Example 24 | 105 | 0.68 | 0.15 | A | A | 84 | 39 | 38 | 38 |
| Com. Ex. 1 | 350 | 0 | 0 | B | C | 22 | 21 | 5 | 11 |
| Com. Ex. 2 | 450 | 0 | 0 | B | C | 33 | 17 | 7 | 8 |
| Com. Ex. 3 | 520 | 0.34 | 0 | B | C | 45 | 19 | 17 | 15 |
| Com. Ex. 4 | 745 | 0.42 | 0 | B | C | 32 | 15 | 11 | 9 |
| Com. Ex. 5 | 240 | 0.58 | 0 | A | C | 27 | 23 | 13 | 14 |
| Com. Ex. 6 | 315 | 0.50 | 0 | A | C | 39 | 19 | 15 | 16 |

Com. Ex.: Comparative Example

As shown in Tables 2-1 and 2-2, it was found that the gas separation membranes in which a siloxane compound layer (protective layer) was not provided on a gas separation layer (dense layer, skin layer) had poor gas permeability and poor gas separation selectivity, and that the gas separation selectivity of each of the gas separation membranes was further decreased under the high-temperature, high-humidity conditions and by toluene exposure. In addition, these gas separation membranes had poor membrane formability (low yield) and poor folding endurance (Comparative Examples 1 and 2).

Even in the cases where a siloxane compound layer was provided on a gas separation layer, a Si ratio of the siloxane compound layer that did not satisfy the specification of the present invention also resulted in poor gas permeability and poor gas separation selectivity. In addition, the gas separation selectivity was further decreased under the high-temperature high-humidity conditions and by toluene exposure. Furthermore, the folding endurance of each of the gas separation membranes was also poor (Comparative Examples 3 to 6).

In contrast, the gas separation membranes of Examples 1 to 24 each had good gas permeability and good gas separation selectivity. Furthermore, these gas separation membranes exhibited high gas permeability and high gas separation selectivity even under the high-temperature high-humidity conditions and even after toluene exposure. In addition, these gas separation membranes had good membrane formability and good folding endurance.

[Example 25] Preparation of Composite Membrane

Preparation of PAN Porous Membrane with Smooth Layer
Preparation of Radiation-Curable Polymer Having Dimethylsiloxane Structure A both-terminal methacrylate-modified polydimethylsiloxane X-22-164E (Compound 1, available from Shin-Etsu Chemical Co., Ltd.) (39 g) and a both-terminal thiol-modified polydimethylsiloxane X-22-167B (Compound 2, available from Shin-Etsu Chemical Co., Ltd.) (10 g) were placed in a 300 mL three-necked flask, and 50 g of n-heptane was further added to the flask to dissolve the polydimethylsiloxanes. The resulting solution was maintained at 50° C. for five hours to prepare a solution of a radiation-curable polymer having a polysiloxane structure.

Preparation of Radiation-Curable Composition

The radiation-curable polymer solution (5 g) was cooled to 20° C. and diluted by adding 95 g of n-heptane. Irgacure 184 (available from BASF) (0.01 g) as a photopolymerization initiator was added to the resulting solution to prepare a radiation-curable composition.

Application of Radiation-Curable Composition to Porous Support and Formation of Smooth Layer The radiation-curable composition was applied, by spin coating, to a polyacrylonitrile (PAN) porous membrane (membrane having a polyacrylonitrile porous membrane disposed on a nonwoven fabric, thickness of membrane including nonwoven fabric: about 180 μm) functioning as a support. Subsequently, the resulting PAN porous membrane was irradiated with UV (Light Hammer 10, D bulb, available from Fusion UV Systems, Inc.) under UV treatment conditions of a UV intensity of 24 kW/m and a treatment time of 10 seconds. Subsequently, the PAN porous membrane after UV irradiation was dried to form, on the porous support, a smooth layer having a thickness of 1 μm and having a dimethylsiloxane structure.

Preparation of Composite Membrane

To a 30 mL brown vial bottle, 0.2 g of cellulose acetate (trade name: L-70, available from Daicel Corporation, acetylation degree 0.55, where the term "acetylation degree" refers to a weight percentage of bonded acetic acid per unit weight) and 20.0 g of tetrahydrofuran were added and mixed, and stirred for 30 minutes. Next, 3 mL of the resulting mixed liquid was applied, by spin coating, onto the PAN porous membrane having the smooth layer thereon and dried at 70° C. for eight hours to form a gas separation layer. Furthermore, 6 mL of the radiation-curable composition used in Example 1 was applied onto the gas separation layer by spin coating to form a siloxane compound layer. As a result, a composite gas separation membrane was prepared. The gas separation layer had a thickness of about 300 nm, and the polyacrylonitrile porous membrane had a thickness of about 180 μm that included the thickness of the nonwoven fabric.

A polyacrylonitrile porous membrane having a molecular weight cut-off of 100,000 or less was used. This porous membrane had a permeability of carbon dioxide at 40° C. and 5 MPa of 25,000 GPU.

Formation of Siloxane Compound Layer

The radiation-curable composition used in Example 1 was applied onto the gas separation layer of the composite membrane by spin coating. Subsequently, the resulting composite membrane was irradiated with UV (Light Hammer 10, D bulb, available from Fusion UV Systems, Inc.) under UV treatment conditions of a UV intensity of 24 kW/m and a treatment time of 10 seconds and then dried at 70° C. for two hours. As a result, a composite membrane (gas separation membrane) that had a gas separation layer and a siloxane compound layer (protective layer) having a thickness of about 0.5 μm and disposed on the gas separation layer was prepared. This protective layer has a structure in which siloxane compounds are linked to each other through —S—CH$_2$CH$_2$— and a structure in which siloxane compounds are linked to each other through —CH$_2$CH$_2$—.

[Comparative Example 7] Preparation of Composite Membrane

A composite membrane (gas separation membrane) was prepared as in Example 25 except that, in Example 25, the protective layer disposed on the gas separation layer was a layer formed by using the same siloxane compound as used in Comparative Example 6.

The composite membranes prepared above were evaluated as in Test Examples 1 to 8. The table below shows the results.

Si ratio=(Si-Kα X-ray intensity after immersion in chloroform)/(Si-Kα X-ray intensity before immersion in chloroform),    Mathematical expression (I)

the organopolysiloxane compound layer has a structure in which organopolysiloxane compounds are linked to each other through a linking group selected from *—O—M-O—*, *—S-M-S—*, *—NR$^a$C(=O)—*, *—NR$^b$C(=O)NR$^b$—*, *—O—CH$_2$—O—*, *—S—CH$_2$CH$_2$—*, *—OC(=O)O—*, *—CH(OH)CH$_2$OCO—*, *—CH(OH)CH$_2$O—*, *—CH(OH)CH$_2$S—*, *—CH(OH)CH$_2$NR$^c$—*, *—CH(CH$_2$OH)CH$_2$OCO—*, *—CH(CH$_2$OH)CH$_2$O—*, *—CH(CH$_2$OH)CH$_2$S—*, *—CH(CH$_2$OH)CH$_2$NR$^c$—*, *—CH$_2$CH$_2$—*, *—C(=O)O$^-$N$^+$(R$^d$)$_3$—*, *—SO$_3^-$N$^+$(R$^e$)$_3$—*, and *—PO$_3$H$^-$N$^+$(R$^f$)$_3$—*, where M represents a divalent to tetravalent metal atom; R$^a$, R$^b$, R$^c$, R$^d$, R$^e$, and R$^f$ each independently represent a hydrogen atom or an alkyl group, the symbol * represents a linking site, the linking group *—CH$_2$CH$_2$—* is formed by a polymerization reaction of compounds having a vinyl group, and the organopolysiloxane compound layer contains 10 to 5,000 ppm of an organic solvent.

TABLE 3

| | Content of organic solvent [ppm, on a mass basis] | Si ratio [mass %] | Content ratio of repeating unit of Formula (5) | Membrane formability [Sample error rate (%)] | Folding endurance | CO$_2$ permeance [GPU] | R$_{CO2}$/R$_{CH4}$ Untreated | After wet heat test | After toluene exposure |
|---|---|---|---|---|---|---|---|---|---|
| Example 25 | 150 | 0.94 | 0 | AA | A | 93 | 41 | 40 | 40 |
| Com. Ex. 7 | 300 | 0.50 | 0 | A | C | 51 | 25 | 15 | 14 |

Com. Ex.: Comparative Example

The above results showed that a good gas separation method, a good gas separation module, and a gas separation apparatus including the gas separation module can be provided by using the gas separation membrane of the present invention.

REFERENCE SIGNS LIST

1: gas separation layer
2: porous layer
3: nonwoven fabric layer
4: siloxane compound layer (protective layer)
5: siloxane compound layer (smooth layer)
10, 20, 30: composite gas separation membrane
6: pore
C: siloxane compound layer
S: gas separation layer (dense layer, skin layer)
P: porous layer (support layer)
40: asymmetric gas separation membrane

What is claimed is:

1. A gas separation membrane comprising:
a gas separation layer containing a cellulose resin; and
an organopolysiloxane compound layer disposed on the gas separation layer,
wherein a Si ratio of the organopolysiloxane compound layer after immersion in chloroform to the organopolysiloxane compound layer before immersion in chloroform, the Si ratio being calculated by Mathematical expression (I), is 0.6 to 1.0, 2. The gas separation membrane according to claim 1, wherein the metal atom M is a metal atom selected from Be, Mg, Ca, Sc, Y, Ti, Zr, V, Cr, Mo, Mn, Fe, Co, Ni, Cu, Zn, B, Al, Ga, and In.

3. The gas separation membrane according to claim 1, wherein the linking group is a linking group selected from *—O-M$^1$-O—*, *—S-M$^1$-S—*, *—O—CH$_2$—O—*, *—S—CH$_2$CH$_2$—*, *—OC(=O)O$^2$, *—CH$_2$CH$_2$—*, and *—C(=O)O$^-$N$^+$(R$^d$)$_3$—*, where M$^1$ represents a metal atom selected from Zr, Fe, Zn, B, Al, and Ga; and R$^d$ represents a hydrogen atom or an alkyl group.

4. The gas separation membrane according to claim 3, wherein the organopolysiloxane compound layer has a structure in which organopolysiloxane compounds are linked to each other through a linking group selected from *—O-M$^1$-O—* and —S-M$^1$-S—* and a structure in which organopolysiloxane compounds are linked to each other through a linking group selected from *—O—CH$_2$—O—*, *—S—CH$_2$CH$_2$—*, *—OC(=O)O—*, *—CH$_2$CH$_2$—*, and *—C(=O)O$^-$N$^+$(R$^d$)$_3$—*.

5. The gas separation membrane according to claim 1, wherein the organopolysiloxane compound layer has at least one structure selected from (a) or (b):

(a) a structure having a structure represented by General formula (1) and a structure represented by General formula (2) or General formula (3), or (b) a structure represented by General formula (4), General formula (1)

General formula (2)

General formula (3)

General formula (4)

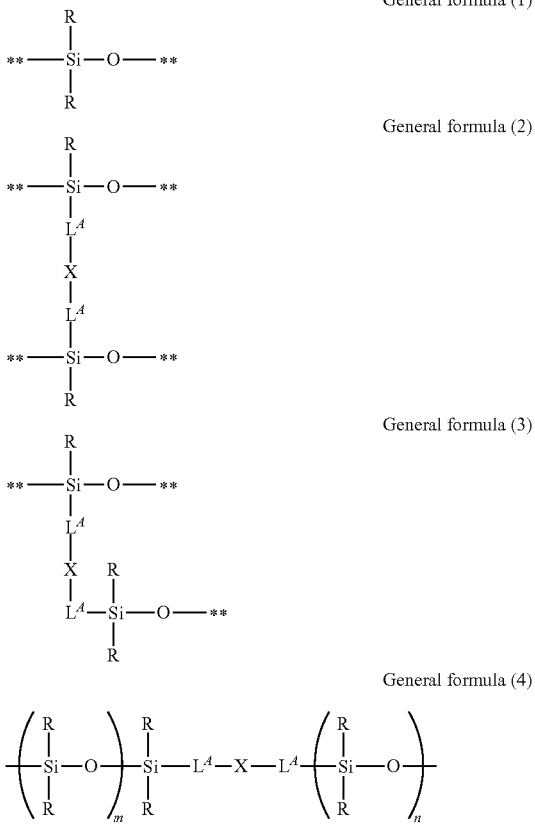

where R represents an alkyl group or an aryl group; $L^A$ represents a single bond or a divalent linking group; X represents a linking group selected from *—O-$M^1$-O—*, *—S-M-S—*, *—O—$CH_2$—O—*, *—S—$CH_2CH_2$—*, *—OC(=O)O—*, *—$CH_2CH_2$—*, and *—C(=O)$O^-N^+(R^d)_3$—* where $M^1$ represents Zr, Fe, Zn, B, Al, or Ga; $R^d$ represents a hydrogen atom or an alkyl group; m and n are each an integer of 2 or more; the symbol * represents a linking site; and the symbol ** represents a linking site in a siloxane bond.

6. The gas separation membrane according to claim 5, wherein the structure of (a) further has a repeating unit represented by Formula (5), Formula (5)

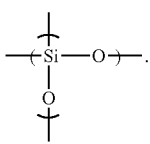

7. The gas separation membrane according to claim 6, wherein a content ratio of the repeating unit represented by Formula (5) in the organopolysiloxane compound layer is 0.01 to 0.55.

8. The gas separation membrane according to claim 1, wherein the metal atom M is B or Al.

9. The gas separation membrane according to claim 3, wherein the metal atom $M^1$ is B or Al.

10. The gas separation membrane according to claim 1, wherein the cellulose resin contained in the gas separation layer is a cellulose resin having a repeating unit represented by Formula (A):

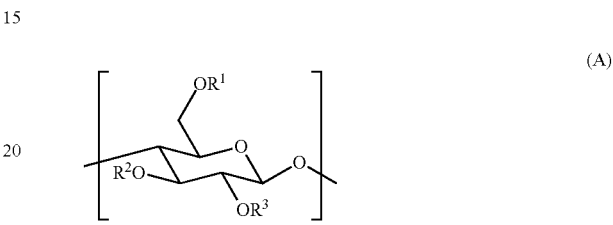

where $R^1$, $R^2$, and $R^3$ each independently represent a group selected from a hydrogen atom, an alkyl group, and an acyl group.

11. The gas separation membrane according to claim 1, wherein the gas separation membrane is an asymmetric membrane.

12. The gas separation membrane according to claim 11, wherein the gas separation membrane has a thickness of 10 to 200 μm.

13. The gas separation membrane according to claim 11, wherein the gas separation membrane is the asymmetric membrane supported by a nonwoven fabric.

14. The gas separation membrane according to claim 1, wherein carbon dioxide is selectively permeated through the gas separation membrane to be separated from gas containing carbon dioxide and methane.

15. A gas separation module comprising the gas separation membrane according to claim 1.

16. A gas separation apparatus comprising the gas separation module according to claim 15.

17. A gas separation method comprising supplying gas to the gas separation membrane according to claim 1.

18. The gas separation method according to claim 17, wherein carbon dioxide is selectively permeated through the gas separation membrane to be separated from methane contained in the gas.

* * * * *